(12) United States Patent
Bayer et al.

(10) Patent No.: US 11,291,774 B2
(45) Date of Patent: Apr. 5, 2022

(54) DRIVE MECHANISM FOR A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 567 days.

(21) Appl. No.: 14/783,552

(22) PCT Filed: Apr. 8, 2014

(86) PCT No.: PCT/EP2014/056981
§ 371 (c)(1),
(2) Date: Oct. 9, 2015

(87) PCT Pub. No.: WO2014/166903
PCT Pub. Date: Oct. 16, 2014

(65) Prior Publication Data
US 2016/0058949 A1   Mar. 3, 2016

(30) Foreign Application Priority Data
Apr. 10, 2013 (EP) .................................. 13163079

(51) Int. Cl.
*A61M 5/315* (2006.01)
*A61M 5/20* (2006.01)
*A61M 5/31* (2006.01)

(52) U.S. Cl.
CPC .......... *A61M 5/3155* (2013.01); *A61M 5/315* (2013.01); *A61M 5/31528* (2013.01);
(Continued)

(58) Field of Classification Search
CPC ............ A61M 5/20; A61M 2005/2026; A61M 2005/314; A61M 5/315; A61M 5/31501;
(Continued)

(56) References Cited

U.S. PATENT DOCUMENTS

2004/0210199 A1   10/2004 Atterbury et al.
2008/0033369 A1*  2/2008 Kohlbrenner ....... A61M 5/3155
                                                      604/207
(Continued)

FOREIGN PATENT DOCUMENTS

CN    101321550    12/2008
JP    2005-508205   3/2005
(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Bhisma Mehta
*Assistant Examiner* — William R Frehe
(74) *Attorney, Agent, or Firm* — Fish & Richardson P.C.

(57) ABSTRACT

The present invention relates to a drive mechanism of a drug delivery device for setting and dispensing of a dose of a medicament, the mechanism comprising: a housing (20), a piston rod (120) to operably engage with a piston (14) of a cartridge (12) to displace the piston (14) in a distal direction (1), a rotatable member (80) arranged on an axially extending axis of rotation (4) in the housing (20), said rotatable member (80) being rotatable in a dose incrementing direction (5) against the action of a spring element (78) and being operably engageable with the piston rod (120) during dose dispensing, a clutch member (150) comprising at least one radially displaceable clutch element (153) to engage with a
(Continued)

rim (82) of the rotatable member (80) with variably adjustable strength.

19 Claims, 16 Drawing Sheets

(52) U.S. Cl.
CPC ..... *A61M 5/31583* (2013.01); *A61M 5/31533* (2013.01); *A61M 2005/2026* (2013.01); *A61M 2005/314* (2013.01); *A61M 2005/3152* (2013.01)

(58) Field of Classification Search
CPC ...... A61M 2005/3152; A61M 5/31525; A61M 5/31526; A61M 5/31528; A61M 5/31533; A61M 5/31548; A61M 5/31565; A61M 5/31576; A61M 5/31578; A61M 5/3158; A61M 5/31581; A61M 5/31583
See application file for complete search history.

(56) References Cited

U.S. PATENT DOCUMENTS

| | | | | |
|---|---|---|---|---|
| 2008/0147005 | A1* | 6/2008 | Moller | A61M 5/31583 604/134 |
| 2009/0275916 | A1* | 11/2009 | Harms | A61M 5/31541 604/506 |
| 2010/0324527 | A1* | 12/2010 | Plumptre | A61M 5/31536 604/500 |
| 2011/0054412 | A1 | 3/2011 | Eich et al. | |
| 2015/0065963 | A1* | 3/2015 | Kjeldsen | A61M 5/31535 604/207 |

FOREIGN PATENT DOCUMENTS

| | | |
|---|---|---|
| JP | 2011-519600 | 7/2011 |
| JP | 2013-506447 | 2/2013 |
| WO | WO 02/092153 | 11/2002 |
| WO | WO 2006/126902 | 11/2006 |
| WO | WO 2007/063342 | 6/2007 |
| WO | WO 2009/135881 | 11/2009 |
| WO | WO 2011/114122 | 9/2011 |
| WO | WO 2012/154110 | 11/2012 |

OTHER PUBLICATIONS

International Preliminary Report on Patentability in International Application No. PCT/EP2014/056981, dated Oct. 13, 2015, 5 pages.
International Search Report and Written Opinion in International Application No. PCT/EP2014/056981, dated May 23, 2014, 9 pages.
"Pen-injectors for medical use—Part 1: Pen-injectors—Requirements and test methods," International Standard, reference No. ISO 11608-1:2000(E), first edition Dec. 15, 2000, 32 pages.

* cited by examiner

A-A

B-B

B-B

DRIVE MECHANISM FOR A DRUG DELIVERY DEVICE

CROSS-REFERENCE TO RELATED APPLICATIONS

This application is a U.S. national stage application under 35 USC § 371 of International Application No. PCT/EP2014/056981, filed on Apr. 8, 2014, which claims priority to European Patent Application No. 13163079.0, filed on Apr. 10, 2013, the entire contents of which are incorporated herein by reference.

The present invention relates to a drive mechanism for a drug delivery device and to a respective drug delivery device. In particular, the invention relates to an injection device such like a pen-type injector inter alia comprising a single and/or a last-dose limiting mechanism and further comprising a comparatively large dose indicating display.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, which is adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected. There already exist some drug delivery devices with end-of-content mechanisms or last dose mechanisms.

Drug delivery devices such like pen type injectors also provide a dose indicating mechanism which is operable to display the size of a set dose to a user. Typically, the housing of such drug delivery devices comprises a dose indicating window in which a number representing the size of the dose shows up.

Especially with elderly patients or users suffering impaired vision, reading of such dose indicating numbers is sometimes difficult. With devices adapted for injection of e.g. insulin, typical dose sizes may vary between 0 and 120 I.U. (International Units) of insulin. Due to the rather compact design and limited geometrical dimensions of typical drug delivery devices the size of such dose indicating numbers is fairly small. For visually impaired persons correct reading of comparatively tiny numbers may therefore be rather difficult. However, since such drug delivery devices are intended for self-medication treatment, it is of importance, that the user is able to correctly determine the size of dose actually set.

OBJECTS OF THE INVENTION

It is therefore an object of the present invention to avoid disadvantages of known drug delivery devices and to provide a drive mechanism of a drug delivery device allowing for an intuitive operation, both for setting and for dispensing of a dose. It is another object to provide a dose indicating mechanism which is easy and unequivocal to read even for persons suffering impaired vision.

In another object, the invention serves to provide a drive mechanism of a drug delivery device for setting and dispensing of a dose of a medicament and further featuring a single and/or a last dose limiting mechanism.

It is a further aim to provide a drug delivery device comprising such a drive mechanism and comprising a cartridge sealed with a piston and being operably engaged with a piston rod of such drive mechanism. The drug delivery device should be rather easy and intuitive to handle.

SUMMARY OF THE INVENTION

In a first aspect a drive mechanism for a drug delivery device is provided for dispensing of a dose of a medicament. The drive mechanism comprises a housing extending in an axial direction. The housing may be of substantially tubular or cylindrical shape that allows gripping and operating of the drive mechanism, hence of the entire drug delivery device by one hand of a user. The housing may also be of rectangular or cubic shape which may smoothly fit into a palm of a user's hand.

The drive mechanism further comprises a piston rod to operably engage with a piston of a cartridge containing the medicament to be dispensed by the drive mechanism. The cartridge comprises a piston, which, by means of a displacement in axial distal direction, serves to expel an amount of the medicament from the cartridge corresponding to the axial displacement of the piston. The piston typically seals the cartridge in axial proximal direction. The piston rod serves to displace the piston of the cartridge in an axial distal direction. The piston rod is therefore operable to apply distally directed thrust or pressure to the piston of the cartridge for displacing the same in distal direction for a predetermined distance that corresponds to a respective amount of the medicament to be dispensed.

The drive mechanism further comprises a rotatable member arranged on an axially extending axis of rotation in the housing. The rotatable member is rotatable in a dose setting direction against the action of a spring element and is further operably engageable with the piston rod during dose dispensing, in which the rotatable member typically rotates in a dose decrementing direction. The rotatable member may comprise an elongated rod or a sleeve extending in axial direction and being rotatably supported in the housing with regard to the axially extending axis of rotation.

The housing of the drive mechanism or the entire drug delivery device may be elongated as well in axial direction. For instance, the drug delivery device may comprise a pen-injector which is intended to be clasped and taken by a user's hand. In typical embodiments the axis of rotation and the elongation of the housing both point in the same direction. The axis of rotation may coincide with the longitudinal direction of the housing, of the cartridge and hence of the piston rod. Coincidence of the axis of rotation with a longitudinal direction of any of the components, housing, piston rod or cartridge means that the axis of rotation extends substantially parallel to the elongation of housing, piston rod or cartridge.

However, in other embodiments the rotatable member, hence the axial direction may extend at a certain angle with respect to the elongation of the housing, the piston rod or the cartridge. It is generally conceivable, that the rotatable member is arranged at a predefined angle with respect to the elongation of the housing. The rotatable member can be for instance implemented in a dose setting member provided and located in a sidewall portion of the housing, thereby extending substantially perpendicular to the longitudinal direction of the housing.

In other embodiments the rotatable member may comprise a component of the drive mechanism operable to transfer angular momentum between a spring-biased drive element, such like a spring element and the piston rod for driving the piston rod in a dose dispensing direction, hence in distal direction with respect to the axial elongation of the housing.

The rotatable member may either directly or indirectly engage with the piston rod during dose dispensing for exerting a driving force to the piston rod by way of which the piston rod can be advanced in distal, hence in dose dispensing direction.

Furthermore, the drive mechanism comprises a clutch member comprising at least one radially displaceable clutch element to engage with an outer rim of the rotatable member with variably adjustable strength. The clutch member is particularly operable to hold and to stop e.g. a spring-induced rotational displacement of the rotatable member. Moreover, the clutch element may not only engage and release with the rotatable member but is further adapted to variably adjust a mechanical interaction, typically a holding or frictional force between a stationary clutch member and the rotatable member.

The clutch member is particularly adapted to apply a holding force of variable size to the outer rim of the rotatable member. Preferably, the clutch member is adapted to exert a gradually or continuously variable force or friction effect onto the outer rim of the rotatable member. In this way, the mechanical resistance the rotatable member experiences by the clutch member can be gradually and/or continuously varied.

In a dose setting mode, the clutch member is preferably operable to provide a holding force so that the rotatable member is secured against an inadvertent returning rotation in a dose decrementing direction, which points in opposite direction compared to the dose setting or dose incrementing direction. In this way, the clutch member serves as a ratchet member allowing the rotatable member to be rotated in dose incrementing direction during dose setting and to inhibit self-acting counter-directed rotation of the rotatable member in a dose decrementing direction.

Typically, the rotatable member is rotatable against the action of the spring element during dose setting. During dose dispensing, the energy stored in the biased spring element is releasable in a controlled way in order to drive the rotatable member in the opposite sense, hence in the dose decrementing direction.

By providing a clutch member which is operable to apply a holding force to the rotatable member with variably adjustable strength or magnitude, the friction or mechanical resistance provided by the clutch member can be individually modified.

In this sense, the clutch member does not only serve to either hold or to release the rotatable member against or with the action of the spring element but provides an effective means to variably release the rotatable member by means of a variable holding force. When in dose dispensing mode, the clutch member at least continuously and gradually releases the rotatable member. Then, a respective rotation may smoothly develop under the action of the spring element.

Here, the spring element is supposed to provide a substantially constant driving force to the rotatable member effective to rotate the rotatable member in the dose decrementing direction. As soon as the holding force of the clutch member equals the driving force of the spring element the rotatable member will start to rotate in dose decrementing direction. With a further gradual decrease of the clutch member's holding force, the angular velocity of the rotatable member may gradually increase accordingly. This way, the clutch member serves to individually modify the angular velocity of the rotatable member for a dose dispensing procedure.

Preferably, the clutch member and in particular the engagement of its clutch element with the outer rim of the rotatable member is controllable by a user of the drug delivery device. In this way, the user himself may individually and intuitively choose a suitable angular velocity of the rotatable member and may therefore determine the velocity of the advancing motion of the piston rod during a dose dispensing procedure.

By means of the clutch member variably adjustable with the rotatable member of the drive mechanism the injection velocity of the drive mechanism can be arbitrarily and gradually modified according to a user's request.

In another embodiment, the clutch element is pivotally supported in radial direction. Here, the radial direction is related to the axis of rotation of the rotatable member which defines the axis of rotation. By having a clutch element pivotally supported in radial direction, by pivoting said clutch element radially inwardly or radially outwardly a decreasing and/or increasing mechanical interaction between the clutch element and the outer rim of the rotatable member can be attained.

Generally, the at least one clutch element of the clutch member may be positioned radially outside the outer rim of the rotatable member. Then, a radially inwardly directed displacement of the clutch element may increase a retarding force effect on the rotatable member.

In an alternative embodiment, the at least one clutch element is arranged radially inside e.g. a hollow-shaped rim of the rotatable member. Then, biasing or stressing the clutch element radially outwardly against the rim of the rotatable member may have a comparable retarding force effect on the rotation of the rotatable member.

Irrespective of the mutual arrangement and the concrete number of clutch elements, the at least one clutch element may be resiliently deformable in radial direction according to a further embodiment. Here, the clutch element may be integrally formed with the clutch member. Preferably, clutch member and clutch element comprise a resiliently deformable thermoplastic material, providing a well-defined elastic modulus.

The mechanical interaction between the at least one clutch element and the rim of the clutch member may be similar to the embodiment with a radially pivotable clutch element. However, a resiliently deformable clutch element is beneficial in terms of mutually assembling the clutch member and the at least one clutch element. In particular, when the at least one clutch element is integrally formed with the clutch member, the number of parts of the drive mechanism can be substantially reduced.

In a further embodiment, the clutch element comprises an arc-shape and at least partially extends along the outer circumference of the outer rim of the rotatable member. Here, it is of particular benefit, when the clutch element comprises a free end section to engage with the rim of the rotatable member in a variably adjustable way. The overall length of the arc-shaped clutch element and the material of the clutch element and/or of the integrally formed clutch member is made of, may precisely determine the resilient properties and the mechanical response of the clutch element in regard of externally applied manipulating or regulating forces.

In a further embodiment, the clutch element comprises a radially inwardly extending lug at a free end portion thereof to engage with the outer rim of the rotatable member. The lug or nose portion at the free end portion of the clutch element provides a well-defined mutual engagement between the outer circumference of the rim and the clutch element. Preferably, the outer rim comprises a specific structure to operably engage with the radially inwardly extending lug of the clutch element. For instance the outer rim may comprise a number of teeth or may be designed as a toothed rim. A toothed structure of the rim may be beneficial to implement a discrete ratchet functionality between the clutch member and the rotatable member, especially during dose setting.

In a further embodiment, the clutch element and the outer rim of the rotatable member are frictionally engageable. Here, the clutch element, in particular it's radially inwardly extending lug and the outer rim of the rotatable member comprise a friction enhancing surface structure. Typically, mutually and directly engaging portions of the clutch element and the outer rim may comprise a well-defined roughness allowing to modify the frictional engagement there between. Moreover, by means of a particular combination of mating materials, a specific friction effect between the clutch element and the rim of the rotatable member can be attained.

In a further but alternative embodiment the clutch element and the rotatable member are positively engageable. Here, the clutch member and the clutch element may substantially implement a ratchet member and a ratchet element, respectively. An outer gearing of the rim may then correspond and engage with a radially inwardly extending geared lug of the clutch element.

Preferably and according to another aspect the clutch element and the outer rim of the rotatable member are frictionally as well as positively engageable. It is for instance conceivable, that application of a maximum holding force by the clutch member to the toothed rim is predominately governed by a purely frictional engagement. As soon as the holding force is gradually decreased, mutually corresponding slopes or edges of e.g. toothed structures of the outer rim and the clutch element may start to frictionally slide with respect to each other.

When matching pair of inter-engaging teeth of the clutch element and of the outer rim, respectively, slip apart so that a neighbouring tooth of e.g. the toothed outer rim consecutively engages with the radially inwardly extending tooth or lug of the clutch element another, and initially friction-based sliding of the next tooth of the outer rim of the rotatable member relative to the lug of the clutch element may take place in a similar way.

The velocity of a mutual slipping of inter-engaging slopes or flanks of a gear rim with the radially inwardly extending lug is predominantly governed and controlled by the force the clutch element is radially inwardly engaged with the rim of the rotatable member. By gradually reducing the radially inwardly directed holding force onto the rotatable member, the velocity of the rotation of the rotatable member relative to the clutch element may increase accordingly.

According to another embodiment, the drive mechanism also comprises a regulating member at least radially enclosing the clutch element and comprising a biasing member to radially engage with the clutch element. The biasing member of the regulating member is displaceable relative to the clutch element in such a way, that a radially inwardly directed force exertable by means of the clutch element onto the outer rim of the rotatable member can be gradually and arbitrarily adjusted.

Here, it is conceivable, that the biasing member itself is radially displaceable in order to modify the radial position, in particular the radial position of the free end of the clutch element relative to the outer rim of the rotatable member. Preferably, the biasing member is assembled and arranged radially outside the clutch element so as to exert a radially inwardly directed force effect onto the clutch member on demand.

The regulating member may comprise a rotatable rod featuring an eccentrically arranged or eccentrically-shaped biasing member. By rotating the regulating member accordingly, a variable radially inwardly directed force effect can be applied to the clutch element on demand.

According to a further embodiment, the regulating member is rotatable relative to the clutch element. In this way, the biasing member can be displaced along the outer circumference of the arc-shaped clutch element. Hence, a position or point of mutual and direct engagement of the biasing member with the clutch element can be arbitrarily modified along the circumference of its arc-shape.

In this way, a radially inwardly acting support for the arc-shaped clutch element can be variably positioned along the outer circumference of the arc-shaped clutch element, hence along its tangential direction. In this way, the effective length or circumference of the arc-shaped clutch element can be modified accordingly thereby effectively modifying the resilient behaviour of the resiliently deformable clutch element.

In a further embodiment, the regulating member is rotatable relative to the clutch element. Here, the regulating member may comprise a sleeve-like shape or sleeve-like geometry. The regulating member, hence the sleeve portion thereof may axially abut with the clutch member. Preferably, the clutch member comprises a cupped-shape with a sidewall portion. In a typical embodiment, the rotatable member, hence its outer rim is enclosed in the cupped receptacle of the clutch member. Moreover, the sleeve of the regulating member may flush and may axially abut with the tubular sidewall portion of the clutch member.

According to a further embodiment, the regulating member comprises an axially extending sleeve portion having at least one inclined groove or slit engaged with at least one axially displaceable pin of a dose dispensing member. The dose dispensing member may comprise a dose dispensing button slidably supported at a proximal end of the housing. For dispensing of a dose, the dose dispensing member may be depressed in distal direction, e.g. by means of a user's thumb. Since the dose dispensing member is axially slidably disposed relative to the housing, the pin of the dose dispensing member is only axially displaceable in a non-rotative way relative to the housing.

Since the groove or slit, effectively serving as a coulisse, extends at a predetermined lead or in an inclined direction relative to the axial direction, hence in an inclined way relative to the axis of rotation of the rotatable member, a purely axially-directed and non-rotative motion of the at least one pin, e.g. invoked by a corresponding distally-directed displacement of the dose dispensing member, leads to a respective rotation of the regulating member relative to the clutch member.

In this way, the biasing member of the regulating member may slide along the arc-shaped clutch element to vary the radially inwardly-directed tension thereof. Depending on the overall geometry and slope of the at least one groove or slit, the rotational behaviour in response of a distally-directed depression of the dose dispensing member or dose dispensing button can be arbitrarily modified.

In effect, depression of the dose dispensing button in distal direction may gradually transfer into a respective angle of rotation of the regulating member and may then be gradually transferred into a respective gradual and radially directed adjustment of the clutch element. In this way, the amount of distally-directed displacement of the dose dispensing button may directly transfer to a varying velocity of a dose dispensing rotation of the rotatable member. Generally, a large displacement path of the dose dispensing member transfers to a comparatively large dispensing velocity.

A rather small displacement path of the dose dispensing member may correlate with a comparatively slow and long-lasting dose dispensing procedure. In this way, the user himself may individually and intuitively decide, on the fly, if the set dose is to be dispensed rather rapidly or in a comparatively slow and long-lasting way.

In a further embodiment, the dose dispensing member is slidably axially displaceable relative to the regulating member against the action of a spring element. Preferably, the spring element may be arranged axially between an inside portion of a proximal end face of the dose dispensing member and a proximal end face of the clutch member. A release of the dose dispensing member may then immediately return the dose dispensing member into its proximal stop position, thereby rotating the regulating member in the opposite sense of rotation. As a consequence, the biasing member will return along the outer circumference of the arc-shaped clutch element to increase the holding force to be exerted by the same on the outer rim of the rotatable member.

Furthermore and according to another embodiment, the mutual engagement of dose dispensing member, regulating member, clutch member and rotatable member is such that an angular velocity of a spring element induced rotation of the rotatable member in a dose dispensing direction is adjustable by the axial displacement of the dose dispensing member relative to the regulating member.

As already described above, axial displacement of the dose dispensing member relative to the regulating member serves to rotate the axially-fixed regulating member in a direction in which the biasing member thereof serves to either decrease or to increase a holding force to be exerted onto the rim of the rotatable member by the clutch element of the clutch member.

In a further embodiment, the position of the at least one groove or slit of the regulating member substantially axially flushes with a radially inwardly extending notch provided at an outer circumference of the clutch member when the dose dispensing member is located in a proximal stop position. In this embodiment, that the at least one radially inwardly extending pin of the dose dispensing member may even leave the groove or slit of the regulating member in axial proximal direction and to enter the radially inwardly extending notch of the clutch member.

In this way, an initial distally-directed displacement of the dose dispensing member at the beginning of a dose dispensing procedure may not yet have an effect on the orientation of the regulating member. During such an initial period of axial displacement, the radially inwardly extending pin would be just axially guided through the axially extending notch of the clutch member. In this way, the dose dispensing member or dose button could be distally displaced for a certain distance before a gradual decoupling of the clutch member is initiated or triggered.

The notch of the clutch member may be further beneficial for a final assembly of the drive mechanism. In this way, the radially inwardly extending pins of the dose dispensing member can be axially and distally guided along and past the clutch member to axially enter groove or slit of the regulating member.

During this initial phase of distally-directed displacement of the dose dispensing member, another clutch mechanism of the drive mechanism, by way of which mechanical energy can be stored in the drive mechanism may operably engage with the piston rod before the rotatable member is released for transmitting angular momentum thereto.

In this way, the additional clutch mechanism, e.g. between a drive sleeve and a drive wheel of the drive mechanism and the mechanical engagement of the clutch member with the rotatable member can be sequentially activated or deactivated for inducing a dose dispensing action. This way it can be ensured, that the mechanical energy to be stored by the spring element does not dissipate in an uncontrolled way. Before the spring element-driven dose decrementing rotation of the rotatable member is released and set free, it is guaranteed, that the rotatable member is operably engaged with the piston rod.

In an alternative embodiment it is also conceivable, that the radially inwardly extending pin of the dose dispensing member is permanently engaged with the regulating member. Here, a similar two-step functionality could be attained by modifying the shape and slope of the regulating member's groove or slit accordingly.

In a further embodiment, the rotatable member comprises a drive spindle rotatably engaged with a rotatable dose setting member for rotating the dose setting member in a dose decrementing direction during dose dispensing. For dose setting, the drive spindle is rotatable in the opposite direction, hence in dose incrementing direction through a well-defined interaction with the dose setting member. The dose setting member may be manually operable by a user and may serve to rotate the drive spindle in a dose incrementing way against the action of the spring element.

Here, the spring element may comprise a helical spring or a compression spring. A helical spring is particularly adapted to directly induce a dose decrementing rotation onto the drive spindle whereas a compression spring to be compressed in axial direction may engage with an axially displaceable drive member threadedly engaged with the drive spindle to form a spindle gear.

Additionally or alternatively, the rotatable member may be implemented as a drive sleeve to be rotated in a dose incrementing direction against the action of e.g. a helical spring. With a variety of conceivable implementations of the rotatable member, e.g. in form of a drive spindle or in form of a drive sleeve it is preferred, that the rotatable member is permanently engaged with a dose indicating arrangement operably to instantly show the size of the actual dose to a user.

During dose setting, the dose indicating arrangement indicates the size of the dose actually set and may typically illustrate a series of increasing dose size indicating numbers when the dose is increased during dose setting. However, during dose dispensing, the previously set and displayed numbers will decrement accordingly until a zero dose configuration at the end of a dose dispensing procedure is reached.

Even though the embodiment as illustrated in the appended Figures only shows a single implementation of the rotatable member with a clutch member, the described and claimed principle of having an adjustable clutch member engaging with a rotatable member can be arbitrarily implemented in a large variety of drive mechanisms for drug delivery devices, such like pen-like injectors.

According to another aspect, the invention also relates to a drug delivery device for dispensing of a dose of a medicament. The drug delivery device comprises a drive mechanism as described above and a cartridge at least partially filled with the medicament to be dispensed by the drug delivery device. The cartridge is arranged in the housing of the drive mechanism or in a cartridge holder of the drug delivery device which is fixed to the housing either releasably or non-releasably, e.g. in case of a reusable or in case of a disposable drug delivery device, respectively. Consequently, the drug delivery device comprises a cartridge holder to receive and to accommodate a cartridge filled with the medicament.

Apart from that, the drug delivery device and the drive mechanism may comprise further functional components, such like a dose injection member, by way of which a user may trigger and control the drug delivery device and its drive mechanism for dispensing of a dose of the medicament.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39), des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38[Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, σ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and σ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and σ have a constant region composed of three tandem Ig domains, and a hinge region for added flexibility; heavy chains μ and σ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCI or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, various embodiments of the invention will be described by making reference to the drawings, in which.

DETAILED DESCRIPTION

Figure 1:
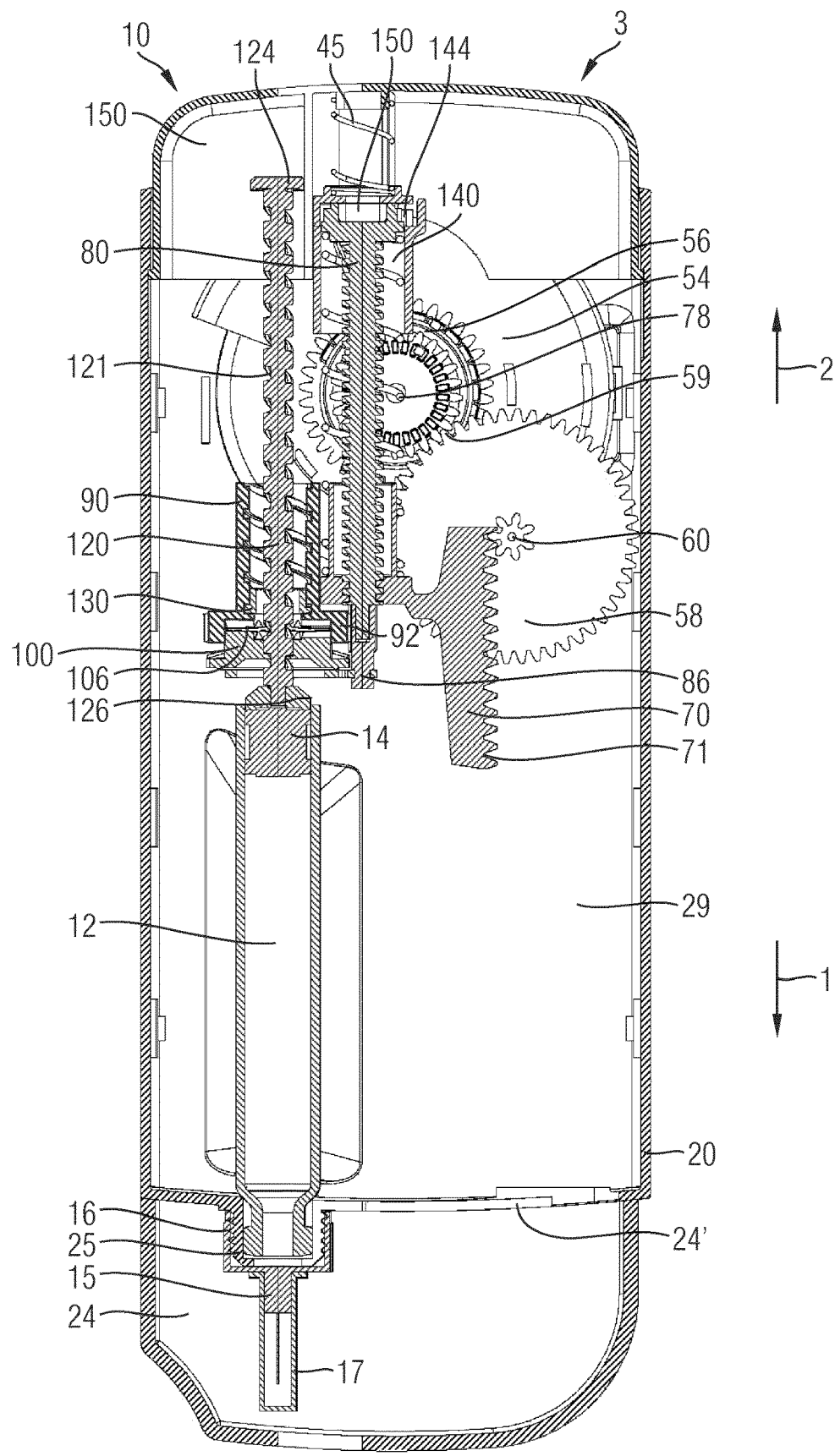
FIG. 1 schematically illustrates a front view of the drug delivery device.
Figure 2:
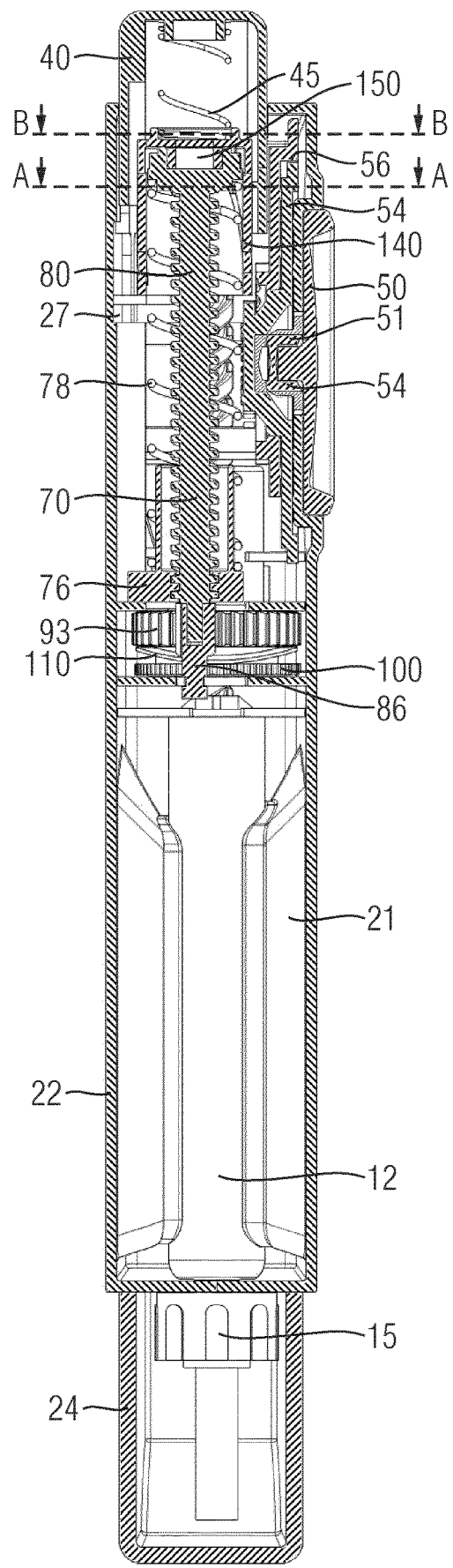
FIG. 2 shows a side view of the drug delivery device.
Figure 3:
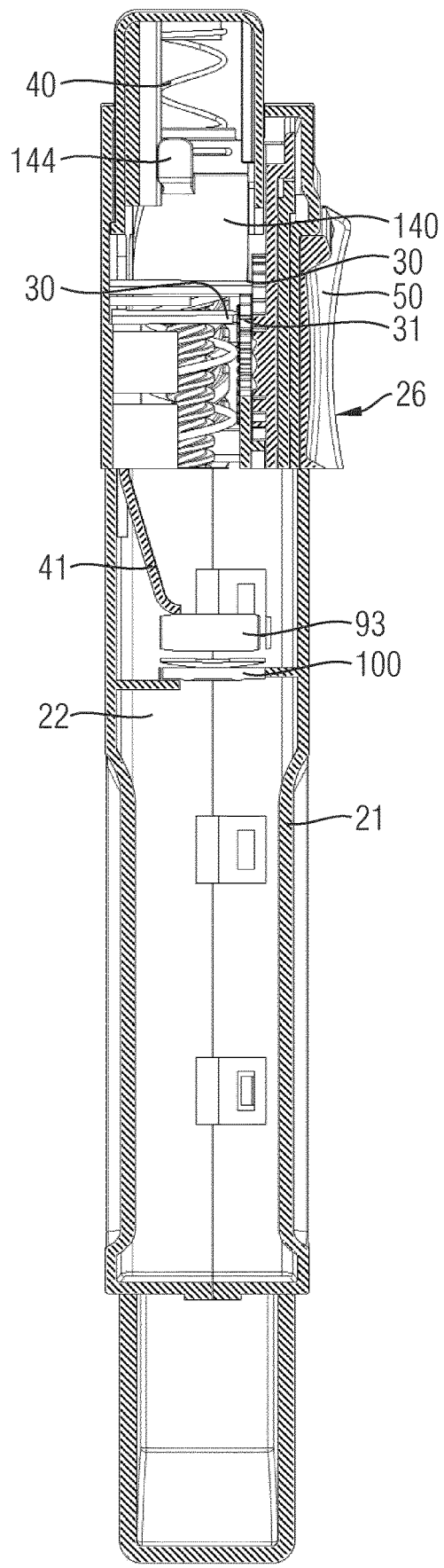
FIG. 3 shows another side view as seen from the opposite side compared to FIG. 2.

As illustrated in FIGS. 1 and 2 the drug delivery device 10 comprises a rather rectangular or cubic-shaped housing 20 comprising an upper housing portion 21 and a lower housing portion 22. In the present embodiment, the upper housing portion 21 may serve as a mounting base to assemble the components of the drive mechanism 3 thereon. The lower housing portion 22 may then serve as a cover, which preferably stabilises and keeps the various components of the drive mechanism 3 at their positions. However, the roles of upper and lower housing portions may also be interchanged in alternative embodiments.

The rectangular shape of the housing 20 is particularly adapted to take and to clasp the device 10 by one hand of a user. The drug delivery device 10 therefore comprises an elongated shape extending in axial direction. In the present context, the axial distal direction is denoted with reference number 1 and the opposite proximal direction is denoted with reference number 2. The housing 20, in particular both of its halves 21, 22, comprises a cartridge window 23.

The cartridge window 23 may comprise a recess in the upper and/or lower housing portion 21, 22 and may be at least partially transparent to allow visual inspection of a filling level of a cartridge 12 assembled inside the housing. The distal end of the housing 20 is further provided and protected by a removable cap 24. The cap 24 may positively engage with a distal end of upper and lower housing portions 21, 22 in order to protect a threaded socket 25 formed by upper and lower housing portions 21, 22.

Figure 6:
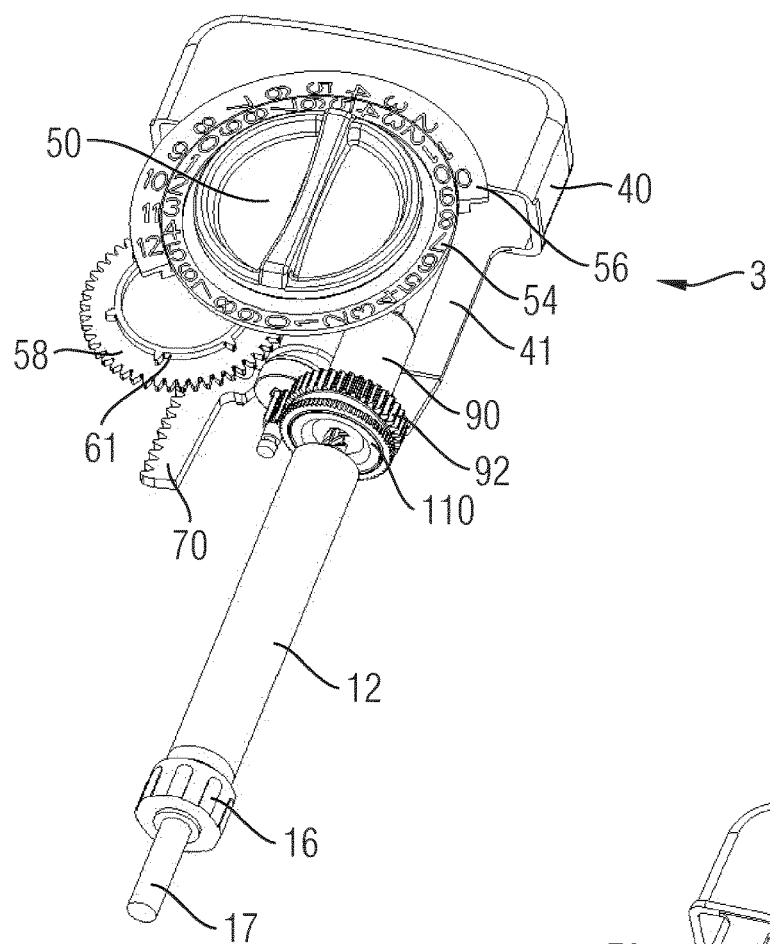
FIG. 6 shows a perspective isolated view of a dose indicating arrangement as seen from the front.
Figure 7:
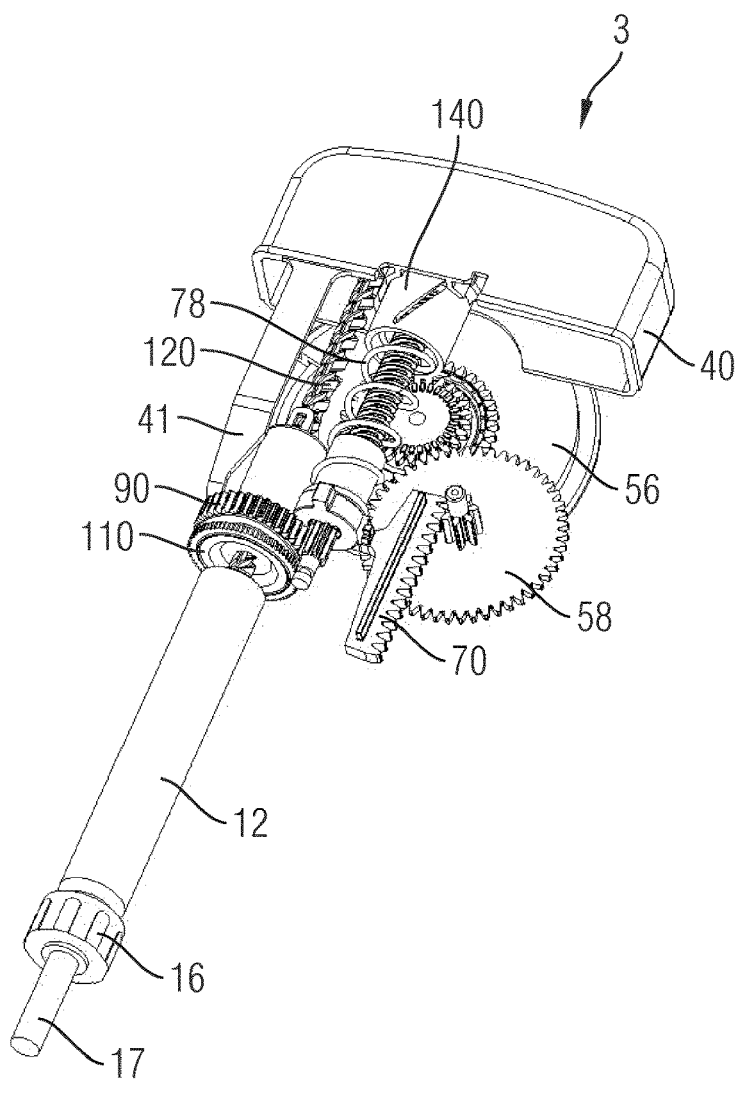
FIG. 7 shows the dose indicating arrangement according to FIG. 6 from the back side.
Figure 8:
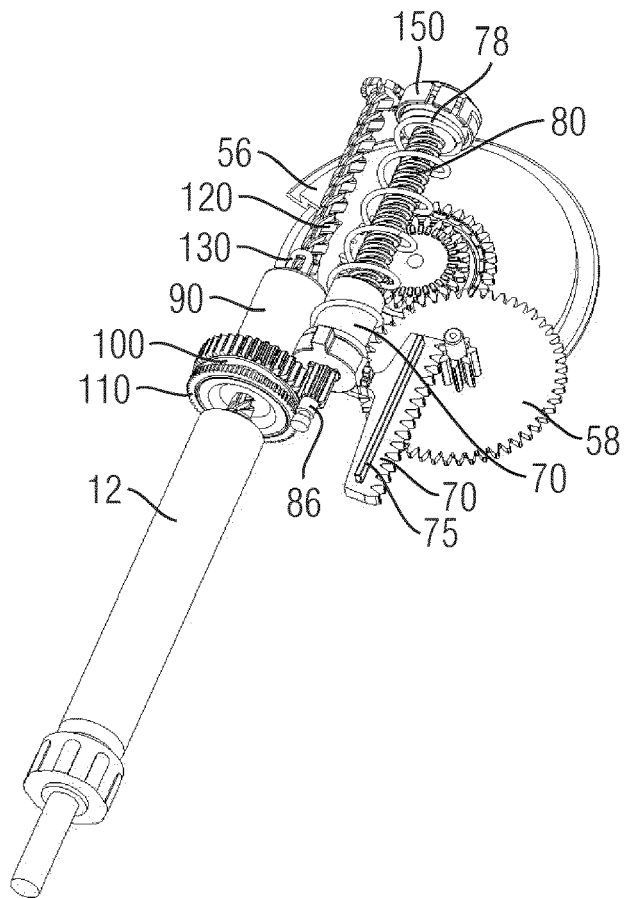
FIG. 8 shows an enlarged view of the dose indicating and dose setting arrangement according to FIG. 7.

The threaded socket 25 is adapted to receive a needle assembly 15, in particular a cup-shaped needle hub 16 providing a double-tipped injection needle. In the various Figures, in particular in FIGS. 1, 2 and in FIGS. 6 and 7, the needle assembly 15 is illustrated with a needle cap 17, which is to be removed from the needle assembly 15 prior to conducting a dose dispensing procedure. The cartridge 12 to be fixed in the housing 20 comprises a tubular-shaped barrel filled with a medicament to be dispensed by the drug delivery device 10.

The barrel is sealed in proximal direction 2 by means of a piston 14, which is slidably disposed in axial direction 1, 2 inside the barrel of the cartridge 12. The piston 14 of the cartridge 12 is operably engageable with a piston rod 120. The piston rod 120 of the drive mechanism 3 is operable to apply distally-directed thrust or pressure to the piston 14 in order to drive the same in distal direction 1. In this way, a fluid pressure may build up inside the cartridge 12.

When the distal dispensing end of the cartridge 12 is connected with the needle assembly 15 in such a way, that a proximally extending tipped portion of the needle penetrates a distally-located seal of the cartridge, e.g. a septum, a predefined amount of the medicament can be expelled from the cartridge 12 via the needle assembly 15 and into biological tissue.

Figure 5:
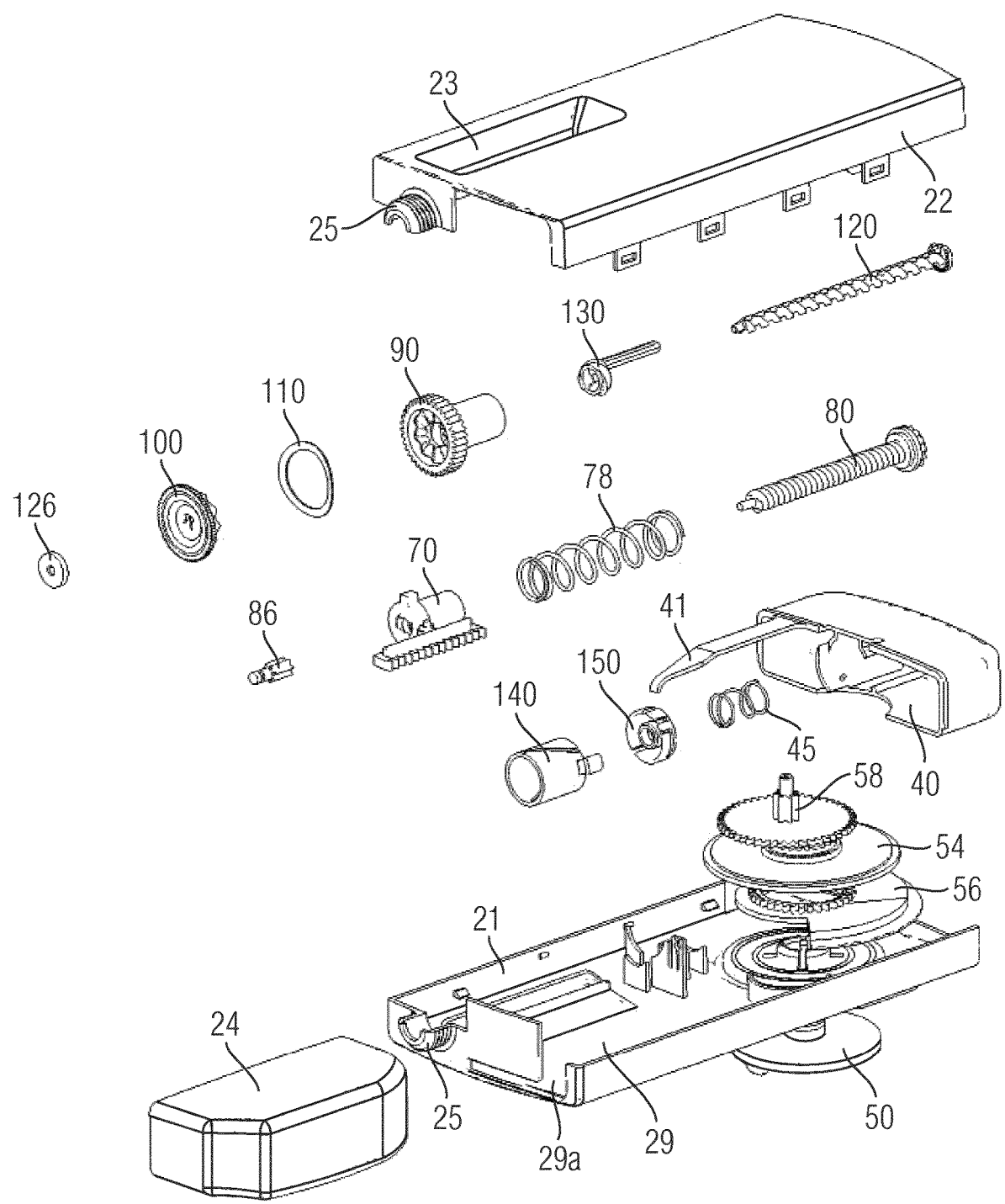
FIG. 5 is an exploded view of the components of the drive mechanism.

As indicated in FIG. 1, the housing 20 comprises a compartment 29 adapted to receive the protective cap 24. For this purpose, the distal end face of the housing 20 comprises a slit 29a as indicated in FIG. 5 allowing to slidably receive the protective cap therein. Here, the slit 29a may serve as a hinge to pivot and to slidably receive the cap 24 when the device is in use. In this way, the cap 24 is non-removably attached to the housing 20 and cannot get lost.

In the following, setting of a dose is described.

For setting of a dose, the user typically takes or clasps the housing 20 in one hand and starts to rotate, in particular to dial a dose setting member 50 located in the upper housing portion 21. The dose setting member 50 as illustrated in detail in FIG. 10 comprises a circular-shaped button comprising an outer rim and a central gripping bar 52 extending across the disc-shaped dose setting member 50. The gripping bar 52 divides the dose setting member 50 into two recesses allowing for an intuitive and easy gripping thereof.

Figure 10:
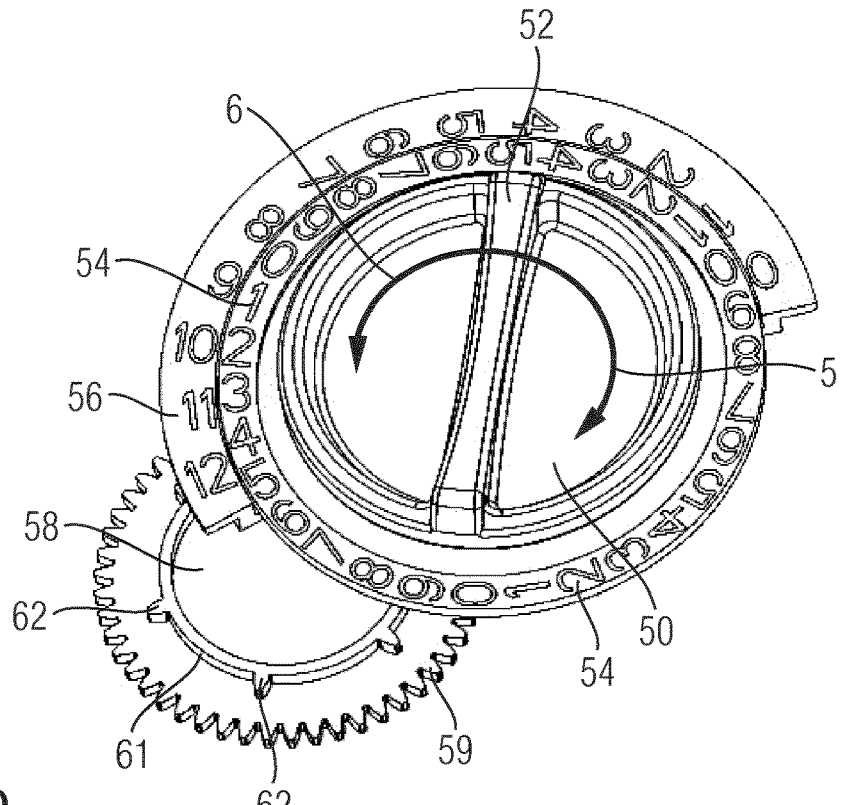
FIG. 10 is an isolated view of the interleaved first and second dose indicating wheels as seen from the front.
Figure 11:
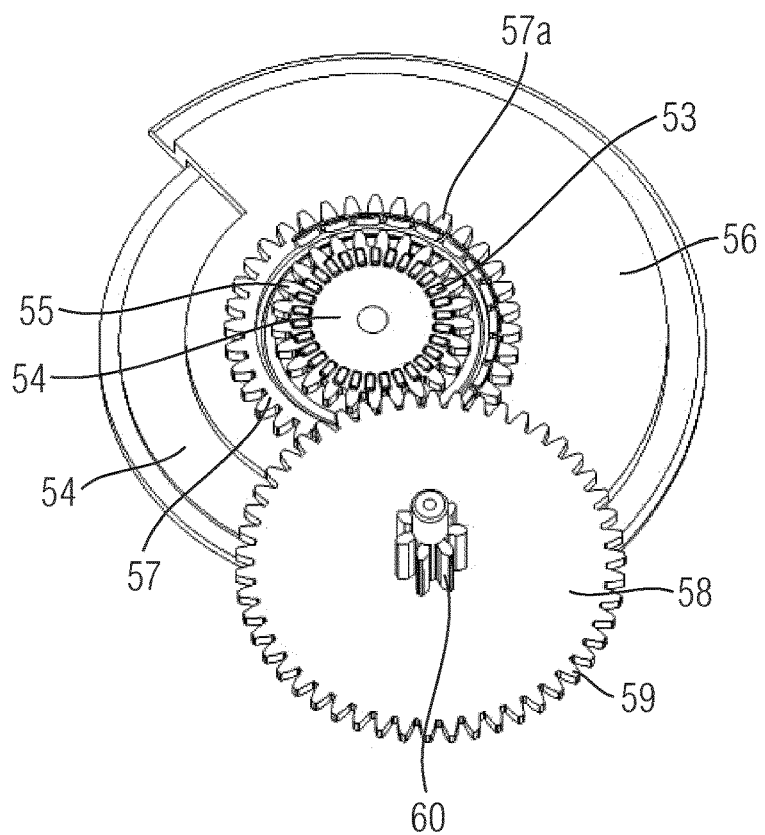
FIG. 11 shows the wheels according to FIG. 10 from the back side.

As indicated by the arrows in FIG. 10, the dose setting member 50 can be rotated either clockwise 5, e.g. in a dose incrementing way or counter-clockwise, e.g. in a dose decrementing way for incrementing or decrementing a dose to be dispensed by the drug delivery device 10. The dose setting member 50 is directly coupled to a dose indicating arrangement as illustrated in FIGS. 10 and 11. The dose setting member 50 as illustrated in cross-section of FIG. 12 is rotatably coupled with a dose indicating wheel 54.

Figure 12:
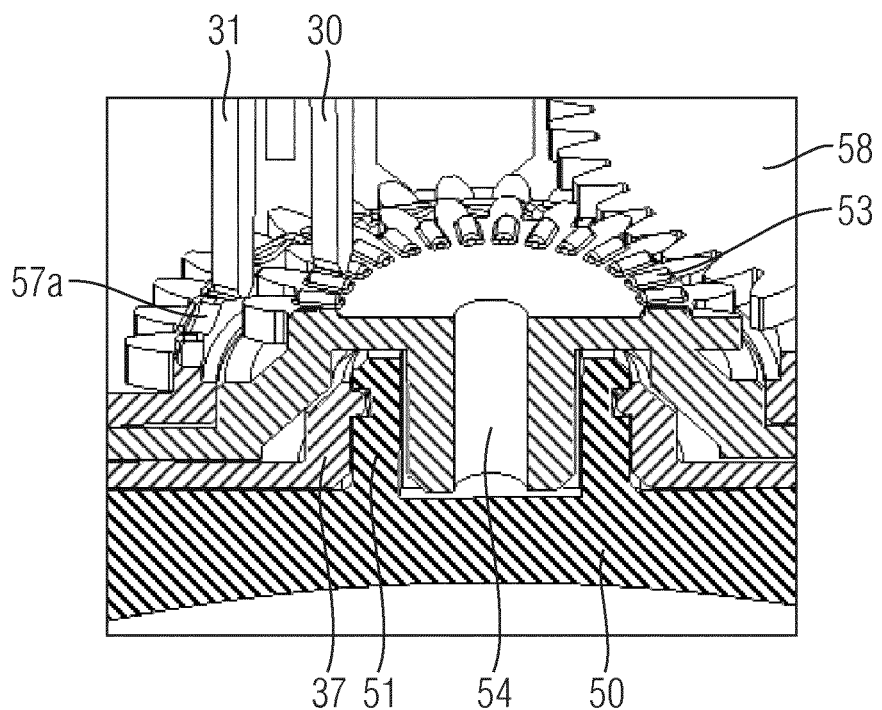
FIG. 12 shows a perspective and partially cut view of the dose indicating wheels assembled in the housing.

As indicated in FIG. 12, the dose indicating wheel 54 comprises an axially extending shaft received in a correspondingly-shaped receptacle of the dose setting member 50. Even though not illustrated, the shaft and the receptacle are splined. Shaft and receptacle of the dose indicating wheel 54 and the dose setting member 50 comprise at least one protrusion engaged with a correspondingly-shaped groove.

As further illustrated in FIG. 12, the receptacle 51 of the dose setting member 54, in particular its sidewall is positively engaged with an inwardly extending fixing rim of the housing 20, thereby fixing the dose setting member 50 in axial direction relative to the housing 20 but allowing the dose setting member 50 to rotate in either direction relative to the housing 20.

The dose indicating wheel 54 serves as a first dose indicating wheel and comprises a series of dose indicating numbers at its outer circumference as illustrated in FIG. 10. Here, the dose setting member 50 and the first dose indicating wheel 54 are coaxially aligned. The dose indicating wheel 54 may feature an outer rim substantially enclosing the outer circumference of the dose setting member 50.

Figure 25:
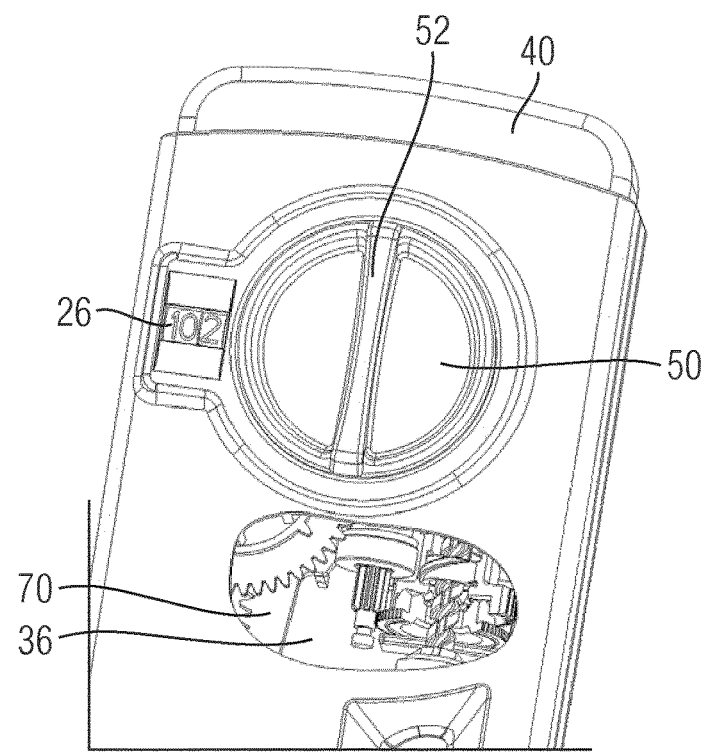
FIG. 25 shows a partially cut view of the assembled drug delivery device.

Due to the splined and direct engagement of the dose setting member 50 and the first dose indicating wheel 54, a rotation of the dose setting member 50 in either direction directly transfers to a respective rotation of the first dose indicating wheel 54. As a consequence, a respective number printed on a side of the dose indicating wheel 54 shows up in a dose indicating window 26 of the housing 20 as illustrated in FIG. 25.

The first dose indicating wheel 54 comprises a sprocket 55 to engage with an outer geared rim 59 of a gear wheel 58. The gear wheel 58 as illustrated in FIG. 11 comprises a further sprocket or pinion 60 axially offset from the geared rim 59 of the gear wheel 58. As will be explained later on, the sprocket 60 is engaged with a toothed rack portion 71 of a drive member 70.

On the side opposite to the sprocket 60 the gear wheel 58 comprises a rim structure 61 featuring isolated and separated cogs 62. Said cogs 62 are operable to engage with a geared rim 57 or sprocket of a second dose indicating wheel 56. As illustrated in FIGS. 10 and 11, the second dose indicating wheel 56 provides a second series of ten digit representing numbers of 10, 20, 30 and so on. By means of the isolated and circumferentially separated cogs 62, a stepwise incrementing rotation of the second dose indicating wheel 56 can be attained when the first dose indicating wheel 54 rotates.

In effect, by means of the two dose indicating wheels 54, 56 all numbers of for instance between 0 and 120 can be illustrated in the dose indicating window 26 of the housing 20. Implementation of the two interleaved dose indicating wheels 54, 56 allows for a rather large scale display so that even persons suffering impaired vision are enabled to read the illustrated numbers.

The first and the second dose indicating wheels 54, 56 further comprise a crown wheel 53, 57a engaging with clicking members 31, 30 provided on the inside of the oppositely disposed housing portion 21. As illustrated in FIG. 12, an inwardly extending pin-shaped clicking member 31 engages with a crown wheel 53 located on a side face of the first dose indicating wheel 54. Correspondingly also the second dose indicating wheel 56 comprises a crown wheel 57a to mate with a correspondingly-shaped clicking member 30 of the housing 20.

Mutual engagement of the first and second dose indicating wheels 54, 56 with respective clicking members 31, 30 provides an audible click sound when the dose setting member 50 is rotated either in dose incrementing direction or in dose decrementing direction. In this way, an audible feedback can be provided to the user when dialling the dose setting member 50 in either direction.

As illustrated for instance in FIGS. 7, 8, 19 and 20 the centrally-located sprocket 60 of the gear wheel 58 meshes with a toothed and elongated rack portion 71 of a drive member 70. The drive member 70 is axially displaceable relative to a rotatable member 80, in the following denoted as a drive spindle 80 extending therethrough. The drive member 70 comprises a sleeve portion 72 to receive the drive spindle 80, which is axially fixed in the housing 20 by means of a bearing 33 as for instance illustrated in FIGS. 13 and 20.

Figure 15:
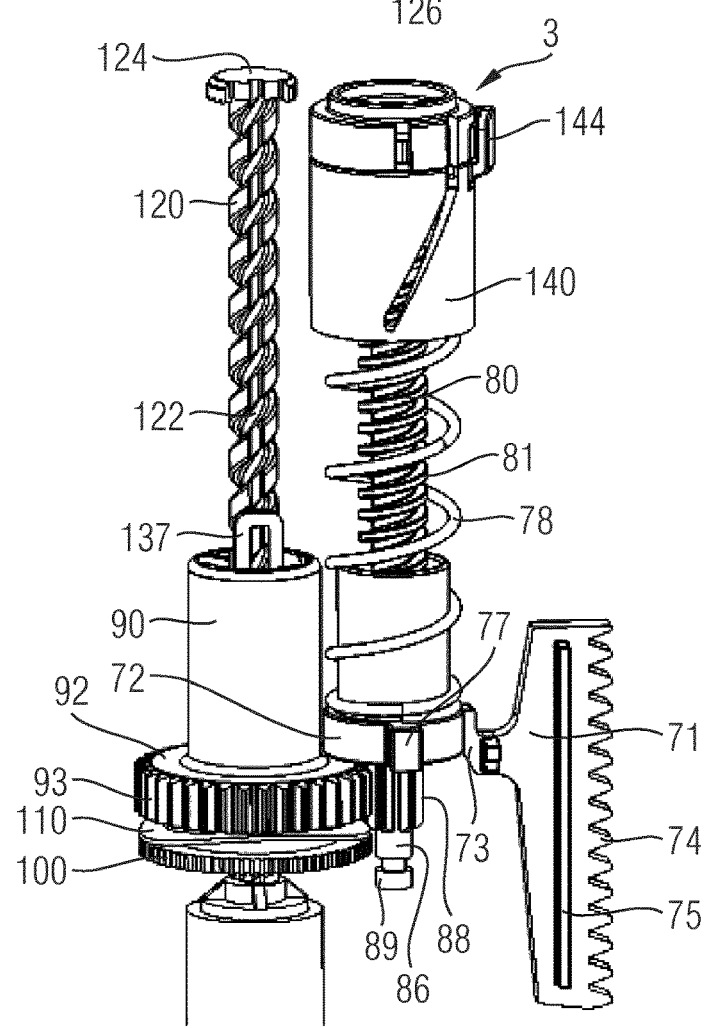
FIG. 15 is a perspective view of the mutual engagement of drive sleeve, drive spindle and drive member.

As illustrated in detail in FIG. 15, the toothed rack portion 71 is connected with the sleeve portion 72 via an interconnecting bar 73. The toothed rack portion 71 therefore radially outwardly extends from the sleeve portion 72 of the drive member 70. The drive member 70 is axially displaceable relative to the drive spindle 80 and relative to the housing 20 against the action of a spring element 78.

As illustrated in FIG. 15, the spring element 78 helically winds around the drive spindle 80. The spring element 78 is preferably designed as a compression spring and can be tensioned by an upward, hence proximally-directed displacement of the drive member 70 relative to the drive spindle 80. As further illustrated in FIG. 15, the sleeve portion 72 of the drive member 70 comprises a radially outwardly extending rim 76 at its distal end, which serves as a distal stop for the spring element 78.

Figure 13:
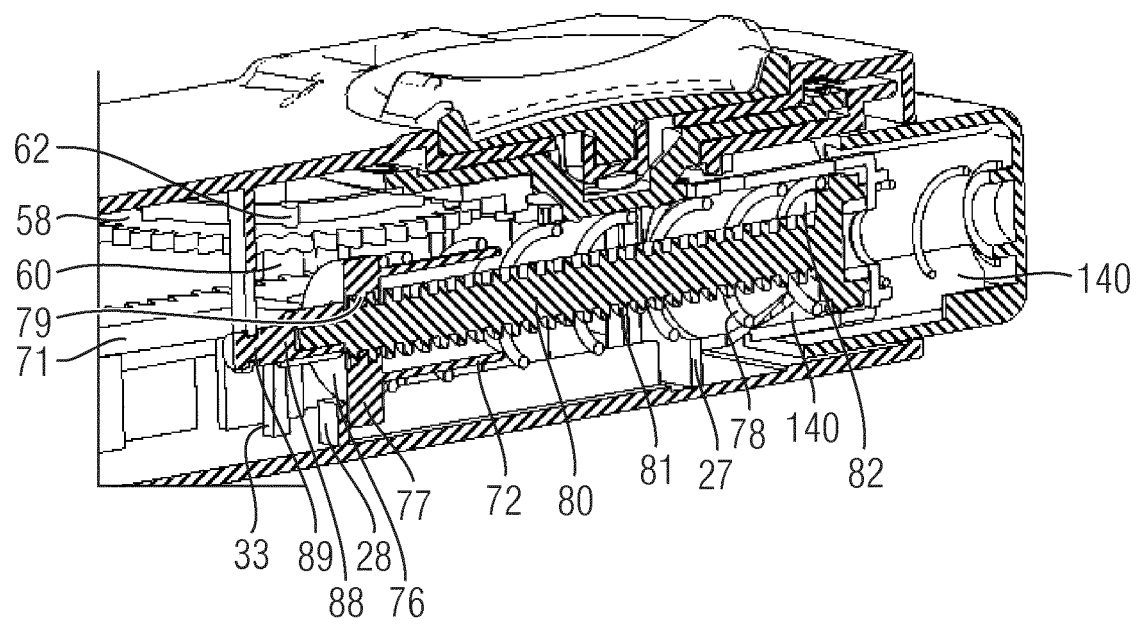
FIG. 13 shows a partially cut and perspective view of the drive spindle arranged in the housing.

Furthermore, the rim 76 comprises a radially outwardly extending protrusion 77 by way of which the drive member 70 can be axially guided relative to the housing 20. Moreover, the protrusion 77 may act as an axial stopper for the drive member 70. As shown in FIG. 13, the housing 20 comprises a proximal stop 27 and a distal stop 28 that are operable to engage with the radially outwardly extending protrusion 77 of the drive member 70. In this way, axial displacement of the drive member 70 relative to the housing 20 can be delimited in distal direction 1 as well as in proximal direction 2.

The drive member 70 is further threadedly engaged with the drive spindle 80. As illustrated in FIG. 13, the flange portion or rim 76 of the drive member 70 comprises an inner thread 79 engaging with an outer thread 81 of the drive spindle 80. Due to this threaded engagement and due to the axial fixing of the drive spindle 80 to the housing 20, a displacement of the drive member 70 in proximal direction 2 against the action of the spring element 78 comes along with a dose incrementing rotation 5 of the drive spindle 80.

Proximally-directed displacement of the drive member 70 relative to the housing 20 can be induced by a dose incrementing rotation of the dose setting member 50 and accordingly by a respective rotation of the gear wheel 58 and its sprocket 60. The axial length of the toothed rack portion 71 typically corresponds to the maximum distance the drive member 70 is allowed to be displaced in distal direction 1 according to the distance of the two stops 27 and 28.

Figure 4:
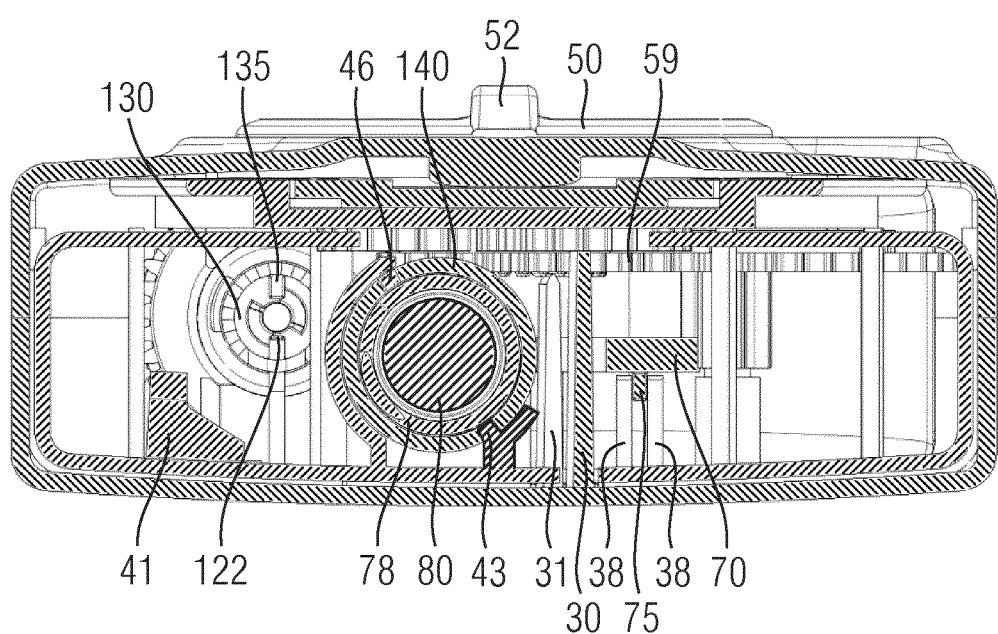
FIG. 4 shows a transverse cross-section through the drug delivery device according to A-A according to FIG. 2.

Additionally, as illustrated in FIGS. 4 and 15, there is provided a protruding ridge portion 75 on the side face of the toothed rack portion 71. Said ridge portion 75 can be guided in a guiding structure 38 of the housing 20 forming an elongated groove supporting the drive member 70 and guiding the drive member 70 in axial direction.

The toothed rack portion 71 comprises consecutive teeth 74 at its lateral side portion to engage with the sprocket 60 of the gear wheel 58.

Figure 9:
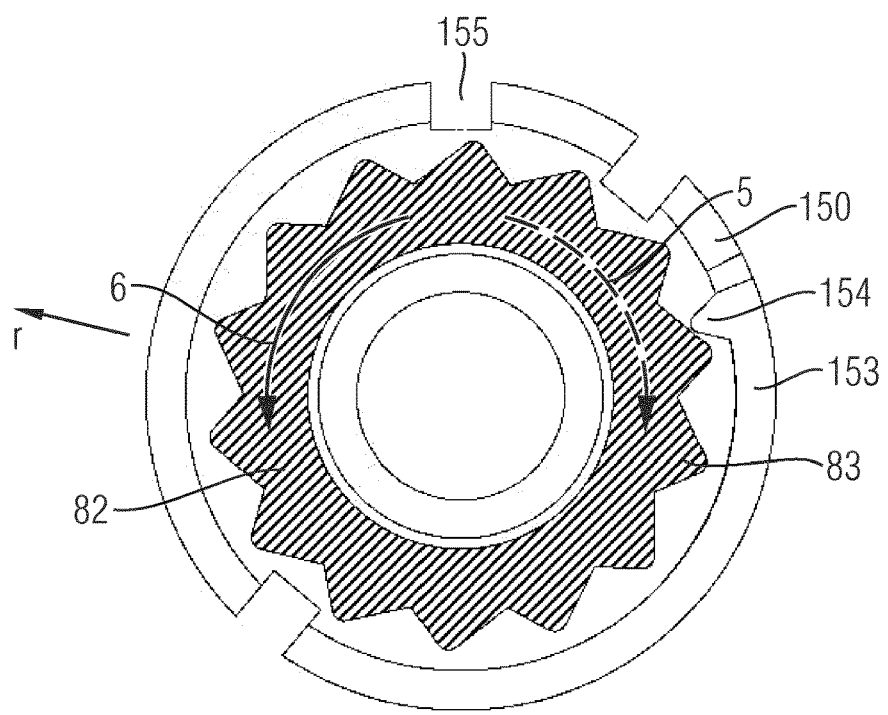
FIG. 9 shows a transverse cross-section B-B according to FIG. 2.

Drive member 70 and drive spindle 80 form a kind of a spindle gear. Proximally-directed displacement of the drive member 70 comes along with a tensioning of the spring element 78 thereby rotating the drive spindle 80 in a dose incrementing direction 5. The drive spindle 80 comprises a toothed rim 82 at its proximal end. As illustrated in cross-section of FIG. 9, said toothed rim 82 engages with a radially outwardly extending latch element 153 of a ratchet member 150. The cup-shaped ratchet member 150 acting as a clutch member 150 receives the toothed rim 82 of the drive spindle 80 and inhibits a counter-directed, hence, a dose decrementing rotation 6 of the drive spindle 80. Moreover, the latch element 153 generally serves as a clutch element 153.

For this purpose, the latch element 153 comprises an arc-shape and at least partially extends along the outer circumference of the toothed rim 82 of the drive spindle 80. The latch element 153 serves as a clutch element and the ratchet member 150 serves as a clutch member to selectively inhibit a rotation of the drive spindle 80. Typically, during dose setting, the latch or clutch element 153 meshes with a radially inwardly extending lug 154 with the teeth 83 of the toothed rim 82.

The latch element 153 is either pivotal in radial direction (r) and/or is resiliently deformable in radial direction to engage with the teeth 83 of the toothed rim 82 of the drive spindle 80. Depending on the slope and geometry of mutually engaging teeth 83 and the lug 154, a dose incrementing rotation 5 as well as a dose decrementing rotation 6 of the drive spindle 80 requires application of a respective actuation force above a predefined level or threshold.

The mutual engagement of the latch element 153 with the toothed rim 82 is in any case sufficient to counterbalance the relaxing force of a biased spring element 78. In this way, the ratchet member 150 is operable to keep the drive spindle 80 fixed, independent of the axial position of the drive member 70 and the degree of tension of the spring element 78.

The spring element 78 may abut with its proximal end at the radially outwardly extending toothed rim 82 of the drive spindle 80. In this way, the spring element 78 is axially constrained between the drive spindle 80 and the drive member 70.

Figure 20:
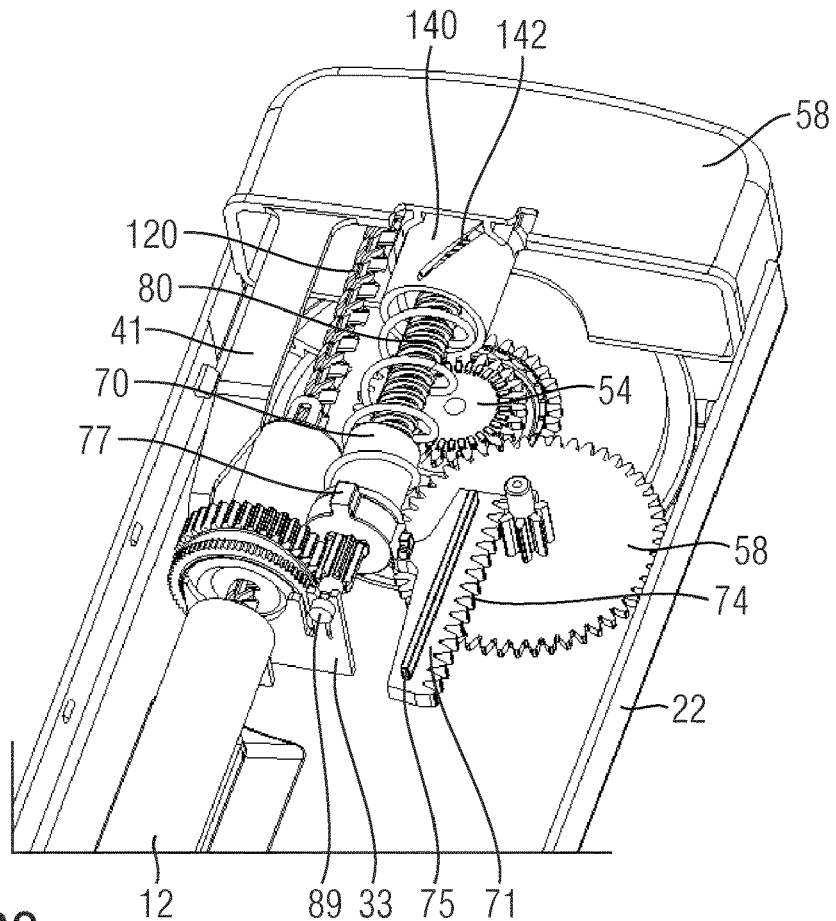

The distal end of the drive spindle 80 is provided with a pinion 86 featuring a bearing portion 89 in form of a circumferential groove or recess. As illustrated in FIGS. 13 and 20, the pinion 86 is supported by a bearing 33 of the housing 20, thereby axially and radially fixing the drive spindle 80 in the housing 20. The pinion 86 comprises various cogs or teeth 88 engaging with a geared rim 93 of a drive sleeve 90. The drive sleeve 90 as illustrated in detail in FIGS. 14 and 15 comprises a tubular-shaped sleeve portion and a radially extending flange portion 92 at its distal end.

The flange portion 92 is provided with a geared rim 93 that meshes with the pinion 86 of the drive spindle 80. Here, drive spindle 80 and drive sleeve 90 are permanently geared. Therefore, a dose incrementing as well as a dose decrementing rotation of the drive spindle 80 always leads to a corresponding rotation of the drive sleeve 90.

Furthermore, the drive sleeve 90 at least partially encloses the piston rod 120. The drive sleeve 90 is operably releasable from the piston rod 120 during dose setting but is operably engageable with the piston rod 120 for dispensing of a dose, as will be explained later on.

Figure 14:
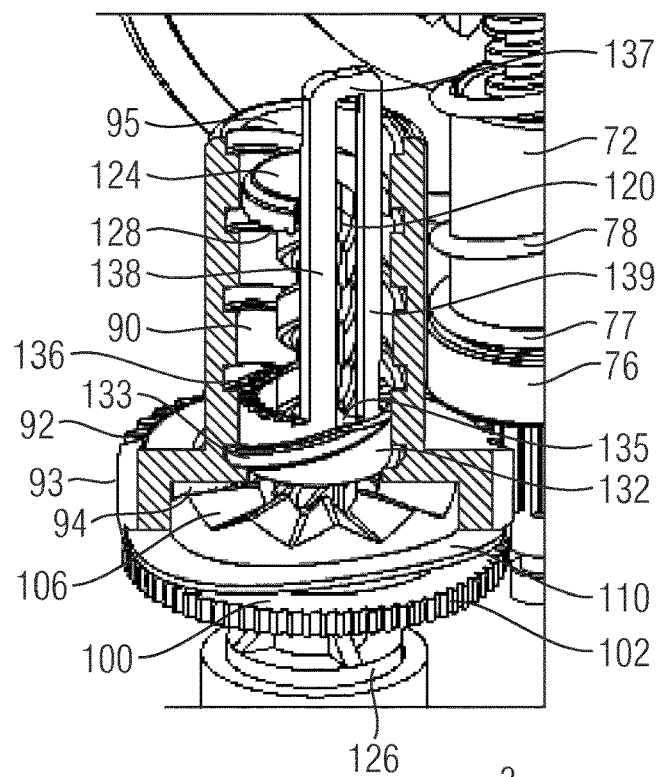
FIG. 14 is a partially cut- and enlarged view of the drive sleeve.

Radially sandwiched between the drive sleeve 90 and the piston rod 120 there is provided a dose limiting member 130. The dose limiting member 130 as illustrated in FIG. 14 comprises a sleeve portion 132 featuring an outer thread 133 engaged with an inner thread 95 of the drive sleeve 90. Moreover, the dose limiting member 130 comprises a proximally extending bracket portion 137 featuring two axially extending and parallely-oriented branches 138, 139 that are mutually interconnected with their proximal ends to form a closed frame structure.

As illustrated for instance in FIG. 15, a proximal end of the bracket portion 137 extends in proximal direction from a proximal end of the drive sleeve 90. By means of the bracket portion 137, the dose limiting member 130 can be rotatably fixed to the housing 20.

For instance, a correspondingly extending pin may protrude through the closed frame structure of the bracket portion 137 in radial direction, thereby effectively inhibiting that the dose limiting member 130 rotates as the drive sleeve 90 is set in rotation by means of the drive spindle 80. Due to the threaded engagement of the dose limiting member 130 and the drive sleeve 90 the dose limiting member 130 experiences a proximally-directed displacement relative to the drive sleeve 90 when the drive sleeve 90 is rotated in a dose incrementing direction 5.

Since a direct mechanical interaction or contact between the drive sleeve 90 and the piston rod 120 is not required, the dose limiting member 130 can be arranged inside the drive sleeve 90 in a rather contactless configuration relative to the piston rod 120, which also extends therethrough. Internal friction of the drive mechanism 3 can therefore be reduced.

Moreover and as illustrated in FIG. 14, the piston rod 120 comprises a stop member 124 which is adapted to engage with the dose limiting member 130 when a maximum number of doses has been dispensed by the drive mechanism 3. In the present embodiment, the stop member 124 of the piston rod 120 comprises a radially outwardly extending flange portion to engage with the proximally-located rim 136 of the sleeve portion 132 of the dose limiting member 130. Preferably, the faces of the stop member 124 and the sleeve portion 132 that face towards each other and which get in direct mutual contact when a last dose configuration is reached comprise a geared structure.

Hence, a distally-facing portion of the stop member 124 may comprise a geared flange, e.g. in form of a crown wheel 128. Correspondingly, also the proximal face of the sleeve portion 132 may comprise a geared rim or a crown wheel portion 136 to mate with the crown wheel 128 of the piston rod 120. Such a configuration may be beneficial with such embodiments, where the piston rod 120 rotates when it is driven in distal direction 1 during dose dispensing.

Mutually engaging crown wheels 128, 136 of the piston rod 120 and the dose limiting member 130 may then immediately inhibit any further rotation of the piston rod 120 relative to the rotatably fixed dose limiting member 130. Said mutual engagement is of particular benefit, when the complete content of the cartridge 12 has been expelled. Then, dose limiting member 130 and piston rod 120 are securely interlocked and effectively impede any further incrementing dose setting.

The dose limiting member 130 effectively serves as a last dose limiter. In an initial configuration of the drive mechanism 3 as for instance illustrated in FIG. 15, the dose limiting member 130 will travel in proximal direction 2 during a dose incrementing rotation of drive spindle 80 and drive sleeve 90. Since the dose setting of a single dose is limited by the axially confined displacement of the drive member 70, the dose limiting member 130 will at maximum reach a proximal end position, in which the sleeve portion 132 still remains in the drive sleeve 90.

In such a configuration the dose limiting member 130 will be separated from the stop member 124 of the piston rod 120. During a consecutive dose dispensing action, the piston rod 120 will advance in distal direction 1 relative to the drive sleeve 90. Since a distally-directed dispensing displacement of the piston rod 120 comes along with a dose decrementing rotation of the drive sleeve 90, also the dose limiting member 130 will return into its initial zero dose configuration as for instance illustrated in FIG. 14.

There may be provided a stop member inside the drive sleeve 90 to provide a well-defined distal stop for the dose limiting member 130. However, such a zero dose stop is not necessarily required for the dose limiting member 130 since the dose decrementing rotation 6 of the drive sleeve 90 is already delimited by the drive member 70 engaging with a distal stop 28 of the housing 20.

With a consecutive dose setting procedure, the dose limiting member 130 will repeatedly displace in axial direction 2. Since the piston rod 120 has moved in distal direction 1 during the previous dose dispensing procedure, the stop member 124 of the piston rod 120 continuously approaches to the axial range in which the dose limiting member 130 is displaceable. If the position of the piston rod 120 corresponds to a dose size smaller than the maximum size of a single dose, e.g. smaller than 120 I.U., the stop member 124 of the piston rod 120 may enter the drive sleeve 90 as for instance illustrated in FIG. 14.

In a proceeding dose setting procedure, the dose incrementing rotation of the drive sleeve 90 is immediately stopped, when the proximally-advancing dose limiting member 130 axially engages with the stop member 124 of the piston rod 120. In this way, it can be assured, that the sum of consecutive doses set and dispensed does not exceed the total amount of doses of the medicament contained in the cartridge 12.

The stop member 124 may comprise a lateral recess in order to receive and to pass by the bracket portion 137 of the dose limiting member 130. Additionally or alternatively, it is also conceivable, that the dose limiting member 130 is splined to the piston rod 120 itself. As for instance illustrated in FIG. 4, the dose limiting member 130 may comprise a radially inwardly extending protrusion 135 to engage with an axially extending groove 122 of the piston rod 120. In this way, the dose limiting member 130 can be rotatably locked to the piston rod 120. In such an alternative embodiment, the piston rod 120 should be rotatably fixed to the housing. Here, the piston rod 120 could be splined to the housing 20.

Figure 16:
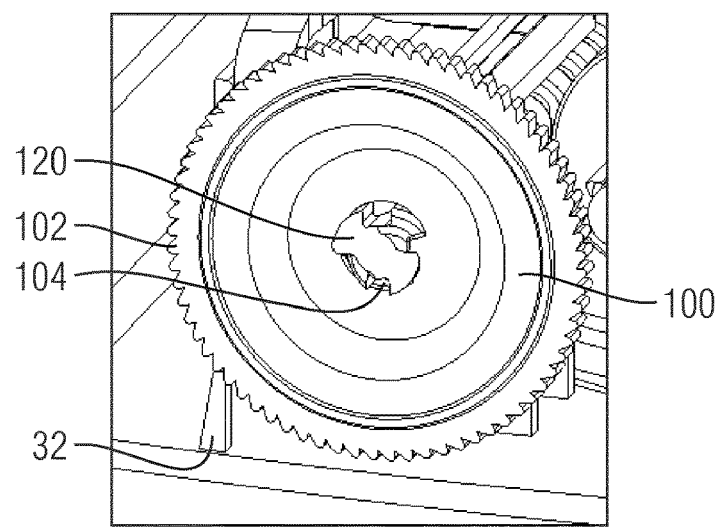
FIG. 16 shows a perspective view of a drive wheel engaged with the piston rod.

In the following dispensing of a dose will be described. For dispensing of a dose the drive sleeve 90 rotates in a dose decrementing direction 6 in such a way, that the torque of the drive sleeve 90 is transferred to a distally-directed displacement of the piston rod 120. As illustrated in FIG. 14, the drive sleeve 90 is coaxially aligned with a drive nut or drive wheel 100. The drive wheel 100 comprises a radially outwardly extending geared rim 102. The teeth of said rim 102 comprise a saw tooth profile and engage with a ratchet member 32 of the housing 20 as illustrated in FIG. 16.

By means of the mutual engagement of the ratchet member 32 with the geared rim 102 rotation of the drive wheel 100 is only allowed in a dose dispensing or dose decrementing direction. A counter-directed movement is effectively blocked and inhibited by said engagement. Moreover, during a dose decrementing or dose dispensing rotation of the drive wheel 100, the ratchet member 32 generates an audible click sound thereby providing an audible feedback to the user, that the injection or dose dispensing is in progress.

The drive wheel 100 further comprises a through opening to receive the piston rod 120 therethrough. The piston rod comprises an outer thread 121 and/or a longitudinally extending groove 122. By means of a groove 122 the piston rod 120 could be rotatably fixed to the housing 20. By means of a threaded engagement of the piston rod 120 with an inner thread 104 of the drive wheel 100, the rotation of the axially fixed drive wheel 100 can be transferred into a distally-directed displacement of the piston rod 120.

In an alternative but not illustrated embodiment, it is also conceivable, that the piston rod 120 is splined to the drive wheel 100 and that the piston rod 120 is threadedly engaged with a housing portion. In such a technically equivalent configuration, rotation of the drive wheel 100 equally transfers into a distally-directed displacement of the piston rod 120 relative to the housing 20 and relative to the barrel of the cartridge 12.

A torque to rotate the drive wheel 100 is provided by the drive sleeve 90, which is axially displaceable between a proximal stop position, in which the drive sleeve 90 is decoupled or disengaged from the drive wheel 100 and hence from the piston rod 120. In its distal stop position, the drive sleeve 90 operably engages with the drive wheel 100 in a torque transmissive way.

As for instance illustrated in FIG. 15, the drive sleeve 90 comprises a radially outwardly extending flange portion 92 at its distal end. From said flange portion 92, there extends a geared rim 93 radially outwardly. The distal end face of the geared rim comprises a ring structure to mate with a correspondingly-shaped flange portion of drive wheel's geared rim 102. Between the rim 102 and the rim 93 there is provided a disc spring 110 which serves to displace the drive sleeve 90 in proximal direction 2.

Hence, drive sleeve 90 and drive wheel 100 can be axially coupled against the action of the disc spring 110 positioned there between. The rim portions 93, 102 of drive sleeve 90 and drive wheel 100 carrying and supporting the disc spring 110 are substantially flat-shaped. In order to transfer angular momentum between the drive sleeve 90 and the drive wheel 100 the drive sleeve 90 comprises a crown wheel portion 94 radially inwardly from the geared rim 93. Correspondingly, the drive wheel 100 comprises a proximally extending socket featuring a correspondingly-shaped crown wheel 106.

When the drive sleeve 90 is displaced in distal direction 1 to get in direct contact with the drive wheel 100, said crown wheels 94, 106 mutually engage and angular momentum acting on the drive sleeve 90 may equally transfer to the drive wheel 100, thereby leading to a distally-directed displacement of the piston rod 120. A distally-directed displacement of the drive sleeve 90 against the action of the disc spring 110 is inducible by a dose dispensing button 40 provided at a proximal end of the housing 20.

Figure 17:
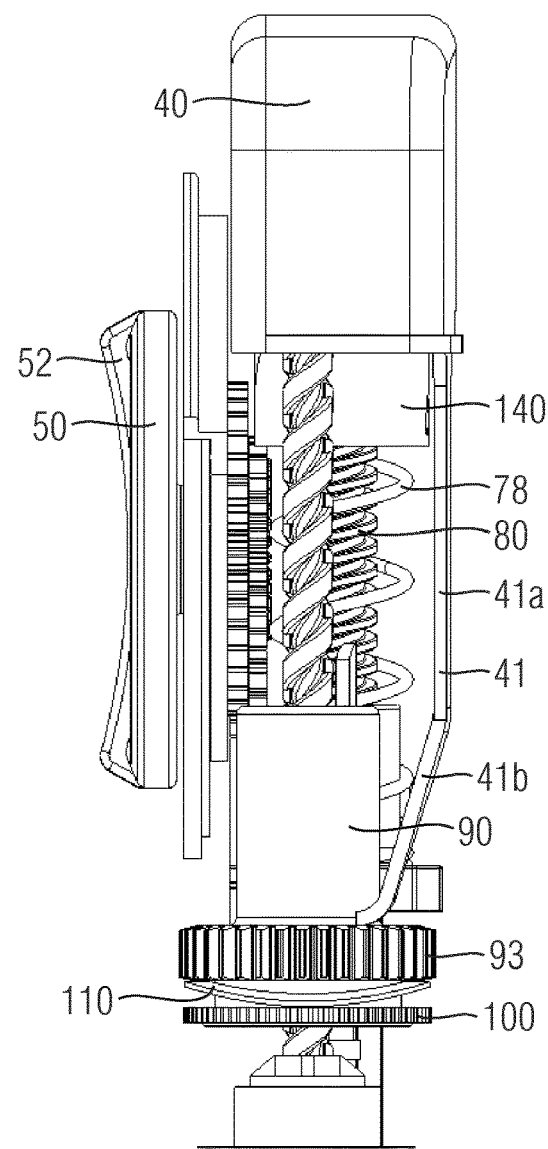
FIG. 17 shows an isolated side view of the drive mechanism without the housing, FIG. 18 schematically shows the mutual interaction of the drive spindle with the drive sleeve.
Figure 18:
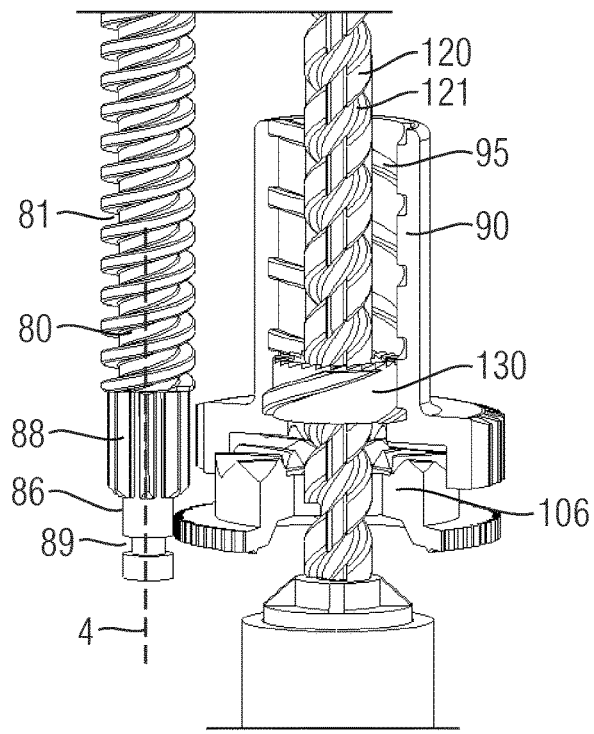
Figure 19:
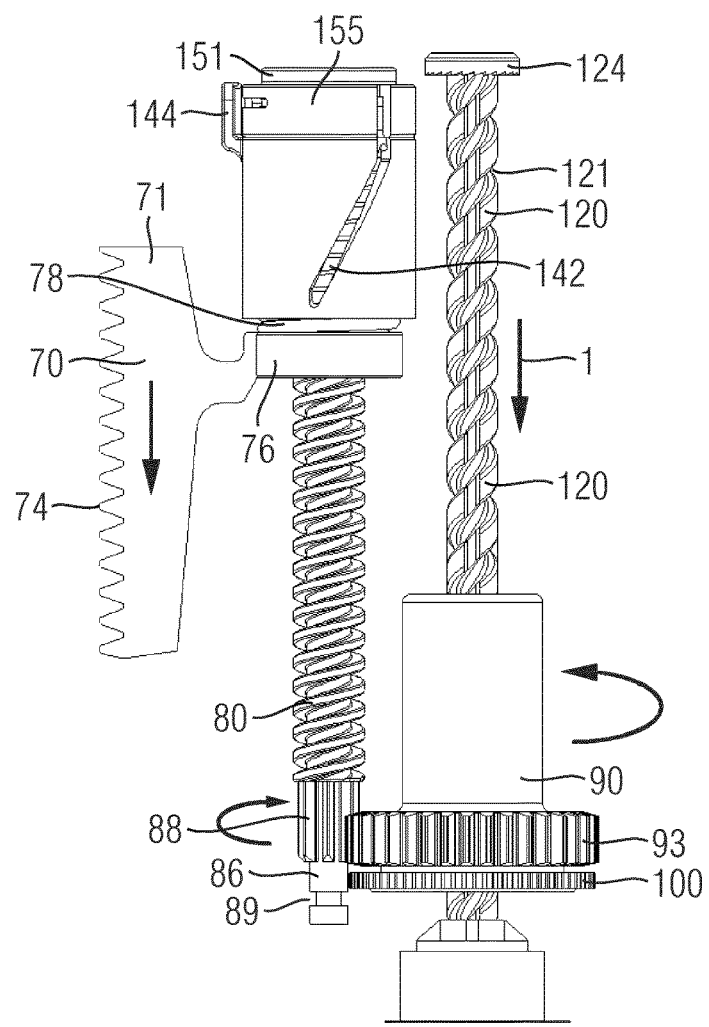
FIG. 19 shows a configuration of the drive mechanism with the drive member in its proximal stop position, FIG. 20 schematically illustrates the assembly of the drive mechanism inside a lower housing portion.

As for instance illustrated in FIG. 17, the dose dispensing button 40 comprises a distally extending strut 41 to but against a proximal-facing portion of the radially outwardly extending flange portion 92 of the drive sleeve 90. The strut 41 comprises a proximal rather axially extending strut portion 41a and a distal strut portion 41b which extends at a predefined angle with respect to the axial direction. In this way, the strut 41 is at least resiliently deformable to a certain degree so that a clutch between the drive sleeve 90 and the drive wheel 100 remains engaged even when the position of the dose dispensing button 40 in axial direction varies to a certain extent.

Depression of the dose dispensing button 40 in distal direction 1 not only engages the drive sleeve 90 and the drive wheel 100. Additionally, distally-directed displacement of the dose dispensing button 40 leads to a release of the drive spindle 80 relative to the ratchet member 150.

Figure 21:
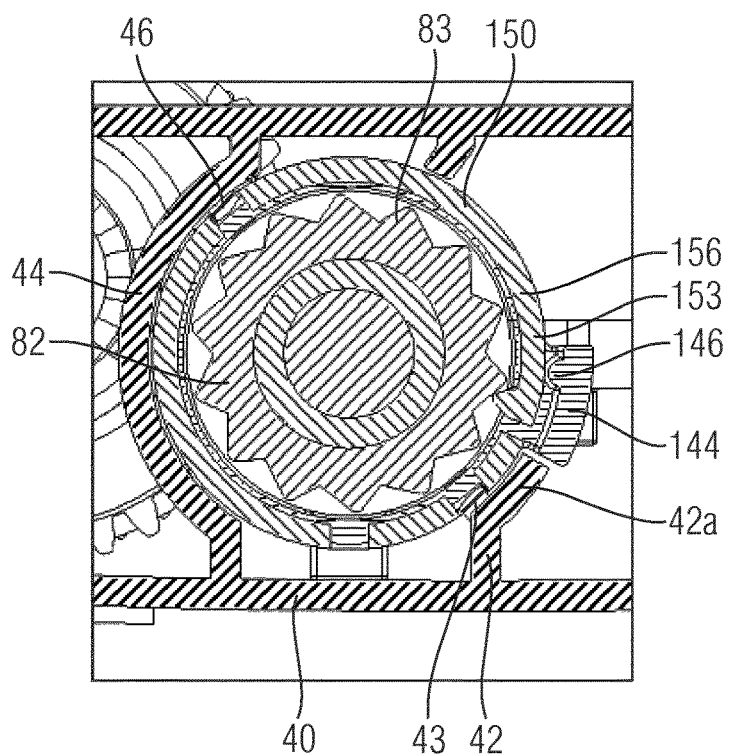
FIG. 21 shows a cross-section along B-B together with the dose dispensing button.
Figure 23:
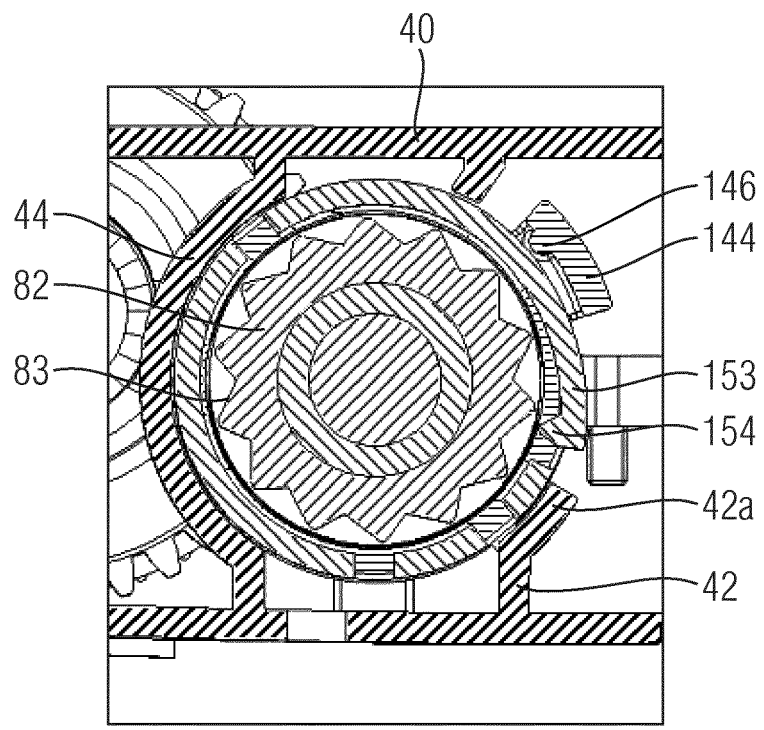
FIG. 23 shows a cross-section B-B according to FIG. 2 with the regulating member in a release configuration.

As becomes apparent from a comparison of FIGS. 21 and 23, the latch element 153 is resiliently deformable in radial direction. As shown in the released configuration according to FIG. 23, the latch element 153 radially protrudes from the outer circumference of the sidewall 156 of the cup-shaped ratchet member 150. In this configuration, the radially inwardly extending lug 154 provided at the free end of the resiliently deformable latch element 153 is no longer engaged with the teeth 83 of the toothed rim 82 of the drive spindle 80.

In the released configuration the drive spindle 80 is effectively free to rotate under the action of the relaxing spring element 78 and the spindle gear of drive spindle 80 and drive member 70 which is driven by said spring element 78.

In the locked or engaged configuration according to FIG. 21, the arc-shaped latch element 153 is biased radially inwardly so that its radially inwardly extending lug 154 engages with the teeth 83 of the drive spindle 80. Radially-directed displacement of the latch element 153 is governed by a biasing member 144 provided at a proximal end of a sleeve-shaped regulating member 140.

Figure 22:
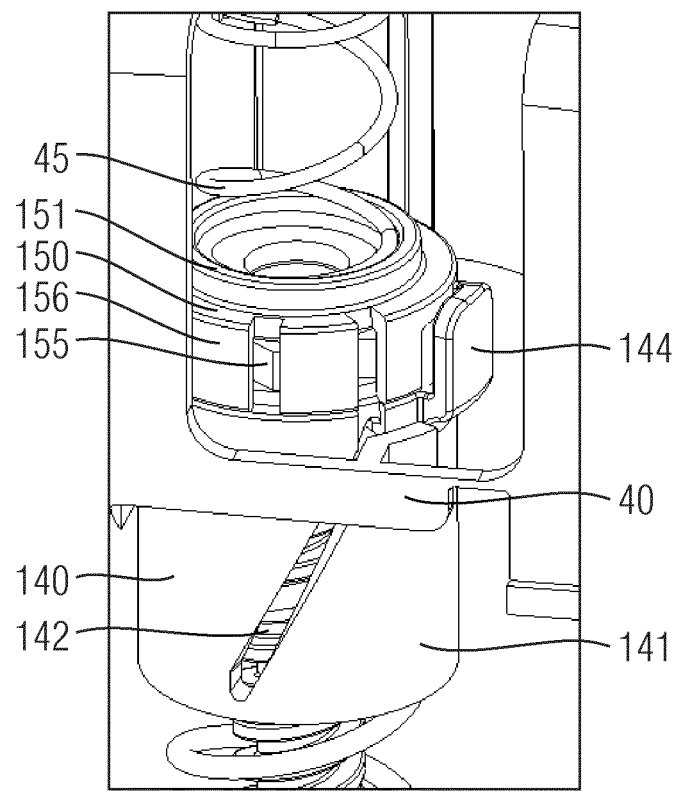
FIG. 22 shows an enlarged perspective view of the mutual engagement of the dose setting button with a regulating member.
Figure 24:
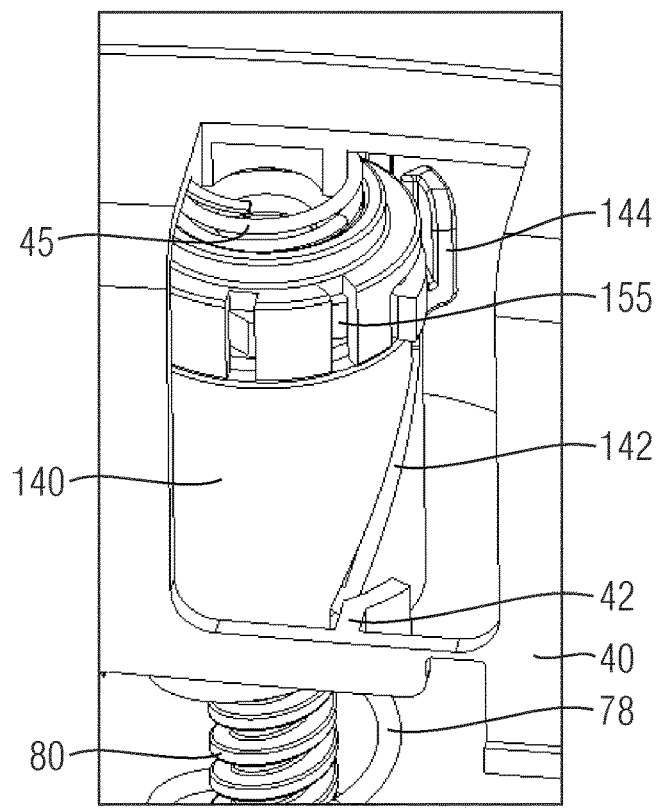
FIG. 24 shows a perspective view according to FIG. 22 with the dose dispensing button fully depressed.

The regulating member 140 is rotatably and coaxially arranged to the ratchet member 150 as for instance illustrated in FIGS. 22 and 24. The regulating member 140 comprises a sleeve portion 141 featuring at least one inclined slit 142 or a respective groove on its outer circumference. As illustrated in FIG. 21 the dose dispensing button 40 comprises an inwardly extending guiding member 42 featuring a radially inwardly extending pin 43 engaging with the inclined slit 142 of the regulating member 140.

Due to the inclined orientation of the slit 142 relative to the axial direction, a distally-directed displacement of the dose dispensing button 40 leads to continuous rotation of the regulating member 140. As a consequence, the biasing member 144 travels along the outer circumference of the arc-shaped latch element 153. Here, the biasing member 144 comprises a radially inwardly extending bulged portion 146 which abuts with an outer circumference of the arc-shaped latch element 153.

In the interlocked configuration, which corresponds to the dose dispensing button 40 in its proximal stop position, the biasing member 144 is fairly close to the free end of the arc-shaped latch element 153. A depression of the dose dispensing button 40 in distal direction 1 comes along with a corresponding rotation of the regulating member 140 and leads to a continuous displacement of the biasing member 144 along the outer circumference of the arc-shaped latch element 153.

As a consequence and as illustrated in FIG. 23, the free end of the latch element 153 may extend radially outwardly. Due to the engagement of the guiding member 42 of the dose dispensing button 40 with the inclined slit 142 of the regulating member 140, the degree of rotation of the regulating member 140 and its biasing member 144 is directly correlated to the degree of axial depression of the dose dispensing button 40.

Due to the resiliently deformable properties of the arc-shaped latch element 153, the holding force provided by the latch element 153 and acting on the toothed rim 82 of the drive spindle 80 can be continuously and steplessly reduced or modified. In this way, mutual friction and gliding behaviour of the latch element 153 and the toothed rim 82 of the drive spindle 80 can be modified in dependence of the depth or degree of axial depression of the dose dispensing button 40.

Depending on the degree of rotation of the regulating member 140, the holding force acting on the drive spindle 80 during an injection procedure can be continuously modified, thereby allowing to regulate the angular velocity of the drive spindle 80 when rotating in a dose decrementing, hence in a dose dispensing orientation 6.

It is to be mentioned here, that the dispensing velocity regulation provided by the mutual interaction of drive spindle 80 and ratchet member 150 can be realized in a variety of different ways. The orientation of the drive spindle 80 serving as a rotatable member and/or the concrete mechanical interaction between the drive spindle 80 and the ratchet member 150 may vary from the illustrated embodiment.

It is only required that the ratchet member 153, generally serving as a clutch member 153, is at least partially radially displaceable with respect to the orientation of the axis of rotation 4 of the drive spindle 80 or of a respective rotatable element 80. Moreover, the mutual retarding interaction of ratchet member 150 and drive spindle 80 can be frictionally based. Additionally, a positive engagement of ratchet member 150 and drive spindle 80 may also exhibit a combined friction-based and positively engaging interaction.

As further illustrated by a comparison of FIGS. 22 and 24, the dose dispensing button 40 is coupled with the proximal end of the ratchet member 150 by means of a spring element 45, e.g. an injection spring 45, typically designed as a compression spring. As further illustrated in FIG. 21 the dose dispensing button 40 is intersected by a strut 44 having a half shell shape which at least partially adopts the outer circumference of the ratchet member 150. In the half shell-shaped portion the strut 44 further comprises an additional pin 46 to engage with a further slit 142 of the regulating member 140.

The regulating member 140 may therefore comprise two oppositely disposed slits 142 to engage with correspondingly arranged radially inwardly extending pins 43, 46 of the dose dispensing button 40. The inwardly extending guiding member 42 of the dose dispensing button 40 further comprises an outer guiding portion 42a, which also adopts the outer shape of the ratchet member 150. By means of the outer guiding portion 42a and the half shell strut 44, the dose dispensing button 40 can be axially guided along the ratchet member 150.

For a secure fastening of the spring element 45, the proximal end of the ratchet member 150 comprises a stepped portion 151 to receive the spring element 45 therein.

As becomes further apparent from FIGS. 21 and 22, the ratchet member 150 comprises axially extended notches 155 that allow to guide the radially inwardly extending pins 43, 46 of the dose dispensing button 40 past the ratchet member 150 during final assembly of the drive mechanism 3.

Depression of the dose dispensing button 40 in distal direction 1 for dispensing of a dose may then be divided into two consecutive steps. In a first step the dose dispensing button 40 is displaced in distal direction by a distance so that the pins 43, 46 advance in distal direction 1 into the slits 142 of the regulating member 140. During this initial displacement the axially extending strut 41 already serves to mutually engage the drive sleeve 90 and the drive wheel 100.

In this way, a torque transmissive coupling of the drive sleeve 90 with the piston rod 120 can be attained even before the drive spindle 80 and hence the drive member 70 are released from the ratchet member 150. It is only due to a further depression of the dose dispensing button 40 in distal direction 1, that the pins 43, 46 run along the slit or groove 142 leading to a releasing rotation of the regulating member 140 and to a gradual and continuous release of the latch element 153. The torque transmissive coupling of drive sleeve 90 and piston rod prior to a release of the drive spindle 80 from the ratchet member can be controlled and governed by the flexural behaviour and by the geometric design of the latch element 153. As already explained above, the depth of depression of the dose dispensing button 40 may determine or may at least influence the angular velocity of the drive spindle 80 during dose dispensing.

Under the action of the relaxing spring element 78, the drive member 70 will return into its initial zero dose configuration. Since the toothed rack portion 71 of the drive member 70 is geared with the sprocket 60 of the gear wheel 58, the dose indicating wheel 54, 56 will count down accordingly. Just before approaching an initial zero dose configuration, the drive member 70 may audibly engage with a clicking member 36 of the housing 20.

Figure 26:
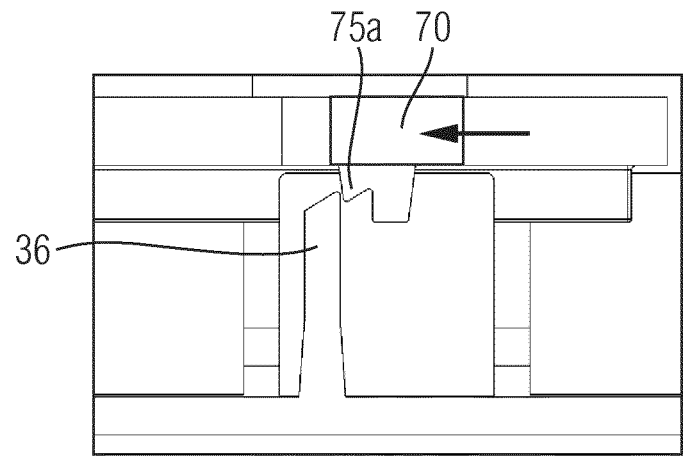
FIG. 26 shows a longitudinal cross-section of the drive member before reaching a zero dose configuration and FIG. 27 is indicative of the drive member reaching the zero dose configuration.
Figure 27:
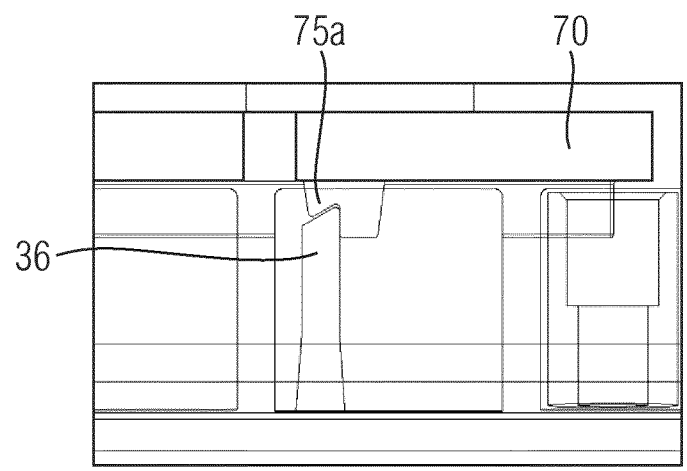

As shown in FIG. 26, the drive member 70 comprises a ledge 75a to engage with an inwardly extending pin-like clicking member 36. Just before reaching a zero dose configuration at the end of a dose dispensing procedure, the bevelled ledge 75a engages with the correspondingly bevelled clicking member 36, thereby generating an audible click sound, in particular when the resiliently deformable clicking member 36 returns into an initial abutment configuration with the bevelled ledge 75a as illustrated in FIG. 27. This audible feedback indicates to the user that a dispensing procedure has terminated.

In the particular and illustrated embodiment, the rotatable member is embodied as a drive spindle 80, the clutch member is represented by a particular ratchet member 150 and the clutch element is embodied as a latch element 153. In particular, every reference made in the following to the drive spindle 80, to the ratchet member 150 and to the latch element 153 correspondingly applies to the rotatable member, to the clutch member and to the clutch element, respectively.

LIST OF REFERENCE NUMERALS 1 distal direction
2 proximal direction
3 drive mechanism
4 axis of rotation
5 dose incrementing direction
6 dose decrementing direction
10 drug delivery device
12 cartridge
14 piston
15 needle assembly
16 needle hub
17 needle cap
20 housing
21 upper housing portion
22 lower housing portion
23 cartridge window
24 cap
25 socket
26 dose indicating window
27 proximal stop
28 distal stop
29 receptacle
29a slit
30 clicking member
31 clicking member
32 ratchet member
33 bearing 36 clicking member
37 fixing rim
38 guiding structure
40 dose dispensing button
41 strut
41a proximal strut portion
41b distal strut portion
42 guiding member
42a outer guiding portion
43 pin
44 strut
45 spring element
46 pin
50 dose setting member
51 receptacle
52 gripping bar
53 crown wheel
54 dose indicating wheel
55 sprocket
56 dose indicating wheel
57 geared rim
57a crown wheel
58 gear wheel
59 geared rim
60 sprocket
61 ring structure
62 cog
70 drive member
71 toothed rack portion
72 sleeve portion
73 bar
74 tooth
75 ridge portion
75a ledge
76 rim
77 protrusion
78 spring element
79 inner thread
80 drive spindle
81 outer thread
82 toothed rim
83 tooth
86 pinion
88 tooth
89 bearing portion
90 drive sleeve
92 flange portion
93 geared rim
94 crown wheel
95 inner thread
100 drive wheel
102 geared rim
104 inner thread
106 crown wheel
110 disc spring
120 piston rod
121 thread
122 groove
124 stop member
126 pressure piece
128 crown wheel
130 dose limiting member
132 sleeve portion
133 outer thread
135 protrusion
136 geared rim
137 bracket portion
138 branch
139 branch
140 regulating member
141 sleeve portion
142 slit
144 biasing member
146 bulged portion
150 ratchet member
151 stepped portion
153 latch element
154 lug
155 notch
156 sidewall

The invention claimed is:

1. A drive mechanism of a drug delivery device, the drive mechanism comprising:
a housing;
a piston rod to operably engage with a piston of a cartridge to displace the piston of the cartridge in a distal direction;
a rotatable member arranged on an axially extending axis of rotation in the housing, the rotatable member being rotatable in a dose incrementing direction relative to the housing against an action of a spring element and being operably engageable with the piston rod during dose dispensing, wherein the spring element is configured to apply a driving force to the rotatable member effective to rotate the rotatable member relative to the housing in a dose decrementing direction opposite to the dose incrementing direction during the dose dispensing; and
a clutch member comprising at least one clutch element to engage with a rim of the rotatable member, wherein the at least one clutch element is at least one of radially displaceable or resiliently deformable in a radial direction relative to the rotatable member, wherein the at least one clutch element radially protrudes from a sidewall of the clutch member, and wherein the at least one clutch element is configured to apply a holding force to the rotatable member with variably adjustable strength or magnitude when the rotatable member is rotated relative to the housing by the spring element in the dose decrementing direction during and for the dose dispensing.

2. The drive mechanism according to claim 1, wherein the at least one clutch element comprises an arc-shape and at least partially extends along an outer circumference of the rim of the rotatable member.

3. The drive mechanism according to claim 1, wherein the at least one clutch element comprises a radially inwardly extending lug at an end portion thereof to engage with the rim of the rotatable member.

4. The drive mechanism according to claim 1, wherein the at least one clutch element and the rim of the rotatable member are frictionally engageable.

5. The drive mechanism according to claim 1, wherein the at least one clutch element and the rotatable member are positively engageable.

6. The drive mechanism according to claim 1, further comprising a regulating member at least radially enclosing the at least one clutch element and comprising a biasing member to radially engage with the at least one clutch element.

7. The drive mechanism according to claim 6, wherein the regulating member comprises an axially extending sleeve portion having at least one inclined groove or slit engaged with at least one axially displaceable pin of a dose dispensing button.

8. The drive mechanism according to claim 7, wherein the spring element is a first spring element, wherein the dose dispensing button is slidably axially displaceable relative to the regulating member against an action of a second spring element.

9. The drive mechanism according to claim 7, wherein mutual engagement of the dose dispensing button, the regulating member, the clutch member, and the rotatable member is such that an angular velocity of a spring element-induced rotation of the rotatable member in a dose dispensing direction is adjustable by an axial displacement of the dose dispensing button relative to the regulating member.

10. The drive mechanism according to claim 7, wherein when the dose dispensing button is located in a proximal stop position, the at least one inclined groove or slit of the regulating member substantially is axially flush with a radially inwardly extending notch provided at an outer circumference of the clutch member.

11. The drive mechanism according to claim 6, wherein the regulating member is rotatable relative to the at least one clutch element.

12. The drive mechanism according to claim 1, wherein the rotatable member comprises a drive spindle rotatably engaged with a rotatable dose setting member for rotating the rotatable dose setting member in at least one of the dose incrementing direction or the dose decrementing direction during at least one of a dose setting or the dose dispensing.

13. The drive mechanism according to claim 1, wherein the clutch member is operable to exert a gradually or continuously variable force or friction effect onto the rotatable member.

14. The drive mechanism according to claim 1, wherein the at least one clutch element is selectively engageable and releasable with the rim of the rotatable member.

15. A drug delivery device comprising:
a cartridge containing a medicament;
a drive mechanism comprising:
a housing;
a piston rod to operably engage with a piston of the cartridge to displace the piston in a distal direction;
a rotatable member arranged on an axially extending axis of rotation in the housing, the rotatable member being rotatable in a dose incrementing direction relative to the housing against an action of a spring element and being operably engageable with the piston rod during dose dispensing; and
a clutch member comprising at least one clutch element to engage with a rim of the rotatable member, wherein the at least one clutch element is at least one of radially displaceable or resiliently deformable in a radial direction relative to the rotatable member, wherein the at least one clutch element radially protrudes from a sidewall of the clutch member, and wherein the at least one clutch element is configured to apply a holding force to the rotatable member with variably adjustable strength or magnitude when the rotatable member is rotated relative to the housing by the spring element in a dose decrementing direction during and for the dose dispensing, wherein the spring element is configured to apply a driving force to the rotatable member effective to rotate the rotatable member relative to the housing in the dose decrementing direction opposite to the dose incrementing direction during the dose dispensing; and
wherein the cartridge is arranged in the housing of the drive mechanism.

16. The drug delivery device according to claim 15, wherein the clutch member is operable to exert a gradually or continuously variable force or friction effect onto the rotatable member.

17. The drug delivery device according to claim 15, wherein the at least one clutch element is selectively engageable and releasable with the rim of the rotatable member.

18. A drive mechanism of a drug delivery device, the drive mechanism comprising:
a housing;
a piston rod to operably engage with a piston of a cartridge to displace the piston of the cartridge in a distal direction;
a rotatable member arranged on an axially extending axis of rotation in the housing, the rotatable member being rotatable in a dose incrementing direction relative to the housing against an action of a spring element and being operably engageable with the piston rod during dose dispensing, wherein the spring element is configured to apply a driving force to the rotatable member effective to rotate the rotatable member relative to the housing in a dose decrementing direction opposite to the dose incrementing direction during the dose dispensing; and
a clutch member comprising at least one clutch element to engage with a hollow-shaped rim of the rotatable member, wherein the at least one clutch element is at least one of radially displaceable or resiliently deformable in a radial direction relative to the rotatable member, wherein the at least one clutch element is arranged radially inside the hollow-shaped rim of the rotatable member and wherein the at least one clutch element is biased or stressed radially outwardly against the hollow-shaped rim of the rotatable member, and wherein the at least one clutch element is configured to apply a holding force to the rotatable member with variably adjustable strength or magnitude when the rotatable member is rotated relative to the housing by the spring element in the dose decrementing direction during and for the dose dispensing.

19. A drug delivery device comprising:
a cartridge containing a medicament;
a drive mechanism comprising:
a housing;
a piston rod to operably engage with a piston of the cartridge to displace the piston in a distal direction;
a rotatable member arranged on an axially extending axis of rotation in the housing, the rotatable member being rotatable in a dose incrementing direction relative to the housing against an action of a spring element and being operably engageable with the piston rod during dose dispensing; and
a clutch member comprising at least one clutch element to engage with a hollow-shaped rim of the rotatable member, wherein the at least one clutch element is at least one of radially displaceable or resiliently deformable in a radial direction relative to the rotatable member, wherein the at least one clutch element is arranged radially inside the hollow-shaped rim of the rotatable member and wherein the at least one clutch element is biased or stressed radially outwardly against the hollow-shaped rim of the rotatable member, and wherein the at least one clutch element is configured to apply a holding force to the rotatable member with variably adjustable strength or magnitude when the rotatable member is rotated relative to the housing by the spring element in a dose decrementing direction during and for the dose dispensing, wherein the spring element is configured to apply a driving force to the rotatable member effective to rotate the rotatable member relative to the housing in the dose decrementing direction opposite to the dose incrementing direction during the dose dispensing; and wherein the cartridge is arranged in the housing of the drive mechanism.

\* \* \* \* \*

UNITED STATES PATENT AND TRADEMARK OFFICE
CERTIFICATE OF CORRECTION

| | |
|---|---|
| PATENT NO. | : 11,291,774 B2 |
| APPLICATION NO. | : 14/783552 |
| DATED | : April 5, 2022 |
| INVENTOR(S) | : Stefan Bayer et al. |

It is certified that error appears in the above-identified patent and that said Letters Patent is hereby corrected as shown below:

In the Claims

Column 27, Line 17, Claim 10, delete "substantially is" and insert -- is --

Signed and Sealed this
Thirty-first Day of May, 2022

Katherine Kelly Vidal
*Director of the United States Patent and Trademark Office*